US010687864B2

(12) United States Patent
Beyar et al.

(10) Patent No.: US 10,687,864 B2
(45) Date of Patent: Jun. 23, 2020

(54) COMPOSITE IMPLANT COATING

(71) Applicant: Carbofix In Orthopedics LLC, Wilmington, DE (US)

(72) Inventors: Mordechay Beyar, Caesarea (IL); Oren Globerman, Kfar-Shemaryahu (IL); Ronen Shavit, Tel-Aviv (IL)

(73) Assignee: Carbofix IN Orthopedics LLC, Wilmington, DE (US)

( * ) Notice: Subject to any disclaimer, the term of this patent is extended or adjusted under 35 U.S.C. 154(b) by 170 days.

(21) Appl. No.: 16/101,591

(22) Filed: Aug. 13, 2018

(65) Prior Publication Data
US 2018/0353219 A1 Dec. 13, 2018

Related U.S. Application Data

(63) Continuation of application No. 14/441,862, filed as application No. PCT/IL2013/050927 on Nov. 11, 2013, now Pat. No. 10,045,798.

(Continued)

(51) Int. Cl.
*A61B 17/70* (2006.01)
*A61B 17/72* (2006.01)
(Continued)

(52) U.S. Cl.
CPC .......... *A61B 17/7059* (2013.01); *A61B 17/72* (2013.01); *A61B 17/80* (2013.01); *A61B 17/8033* (2013.01); *A61B 17/866* (2013.01); *A61L 31/082* (2013.01); *A61L 31/10* (2013.01); *A61L 31/126* (2013.01); *A61L 31/18* (2013.01);
(Continued)

(58) Field of Classification Search
CPC ............ A61B 17/7059; A61B 17/8033; A61B 17/866
See application file for complete search history.

(56) References Cited

U.S. PATENT DOCUMENTS 3,905,777 A * 9/1975 Lacroix ............... A61F 2/28
428/550
4,662,887 A * 5/1987 Turner ............... A61B 17/80
623/23.58

(Continued)

FOREIGN PATENT DOCUMENTS

CA 1332098 9/1994
EP 0169001 1/1986
(Continued)

OTHER PUBLICATIONS

International Preliminary Report on Patentability dated May 21, 2015 From the International Bureau of WIPO Re. Application No. PCT/IL2013/050927.

(Continued)

*Primary Examiner* — Christian A Sevilla

(57) ABSTRACT

A coating layer, for example PEEK or titanium foil, shields a bone implant surface from wearing interactions with surfaces of bone and/or other implants. The coating prevents shedding particles which are difficult to distinguish from evidence of potentially dangerous conditions, for example, microorganism contamination and/or degenerating tissue. Methods and structures for securing a coating layer are described. Other uses and implementations of coating layers are described.

23 Claims, 18 Drawing Sheets

Related U.S. Application Data

(60) Provisional application No. 61/841,966, filed on Jul. 2, 2013, provisional application No. 61/724,983, filed on Nov. 11, 2012.

(51) Int. Cl.

| | | |
|---|---|---|
| *A61B 17/80* | (2006.01) | |
| *A61B 17/86* | (2006.01) | |
| *A61L 31/08* | (2006.01) | |
| *A61L 31/10* | (2006.01) | |
| *A61L 31/12* | (2006.01) | |
| *A61L 31/18* | (2006.01) | |
| *A61B 17/00* | (2006.01) | |

(52) U.S. Cl.
CPC . *A61B 2017/00526* (2013.01); *A61L 2420/08* (2013.01); *A61L 2430/02* (2013.01)

(56) References Cited

U.S. PATENT DOCUMENTS

| | | | |
|---|---|---|---|
| 4,750,905 A | 6/1988 | Koeneman et al. | |
| 4,978,360 A | 12/1990 | Devanathan | |
| 5,009,664 A | 4/1991 | Sievers | |
| 5,064,439 A | 11/1991 | Chang et al. | |
| 5,181,930 A | 1/1993 | Dumbleton et al. | |
| 5,397,358 A | 3/1995 | Wenner et al. | |
| 7,419,714 B1 * | 9/2008 | Magerl | A61B 17/80 |
| | | | 428/131 |
| 7,641,676 B2 * | 1/2010 | Mathieu | A61B 17/8052 |
| | | | 606/287 |
| 8,158,245 B2 | 4/2012 | Pratte et al. | |
| 8,709,055 B2 * | 4/2014 | Beyar | A61B 17/1631 |
| | | | 606/301 |
| 2003/0135275 A1 * | 7/2003 | Garcia | A61F 2/4455 |
| | | | 623/17.11 |
| 2004/0133207 A1 * | 7/2004 | Abdou | A61B 17/7059 |
| | | | 623/16.11 |
| 2006/0052880 A1 * | 3/2006 | Brosnahan, III | A61F 2/30767 |
| | | | 623/23.39 |
| 2007/0055251 A1 * | 3/2007 | Huebner | A61B 17/8047 |
| | | | 606/279 |
| 2007/0123884 A1 | 5/2007 | Abdou | |
| 2007/0213828 A1 * | 9/2007 | Trieu | A61B 17/8042 |
| | | | 623/17.11 |
| 2008/0269893 A1 * | 10/2008 | Bhatnagar | A61B 17/7208 |
| | | | 623/11.11 |
| 2008/0312698 A1 * | 12/2008 | Bergeron | A61B 17/7007 |
| | | | 606/280 |
| 2009/0062862 A1 * | 3/2009 | Perrow | A61B 17/8047 |
| | | | 606/280 |
| 2012/0059376 A1 * | 3/2012 | Rains | A61B 17/72 |
| | | | 606/62 |
| 2013/0060337 A1 * | 3/2013 | Petersheim | A61B 17/808 |
| | | | 623/17.16 |
| 2015/0289911 A1 | 10/2015 | Beyar et al. | |

FOREIGN PATENT DOCUMENTS

| | | |
|---|---|---|
| EP | 0551574 | 7/1993 |
| WO | WO 02/04038 | 1/2002 |
| WO | WO 2006/038056 | 4/2006 |
| WO | WO 2010/082183 | 7/2010 |
| WO | WO 2011/154891 | 12/2011 |
| WO | WO 2014/072983 | 5/2014 |

OTHER PUBLICATIONS

International Search Report and the Written Opinion dated Mar. 5, 2014 From the International Searching Authority Re. Application No. PCT/IL2013/050927.
Invitation to Pay Additional Fees dated Jan. 26, 2014 From the International Searching Authority Re. Application No. PCT/IL2013/050927.
Official Action dated Oct. 20, 2017 From the US Patent and Trademark Office Re. U.S. Appl. No. 14/441,862. (11 pages).
Restriction Official Action dated Jul. 26, 2017 From the US Patent and Trademark Office Re. U.S. Appl. No. 14/441,862. (7 pages).
Supplementary European Search Report and the European Search Opinion dated Nov. 2, 2015 From the European Patent Office Re. Application No. 13854162.8.
Allegheny Technologies "ATI Ti-6AI-4V, Grade 5. Titanium Alloy", Allegheny Technologies Incorporated, ATI, Technical Data Sheet, Version 1, 4 P., Jan. 31, 2012.
Azam et al. "Coatings on Composites", Lappeenranta University of Technology, Faculty of Technology, Department of Mechanical Engineering, Advanced Surface TEchnology Research Laboratory, Mikkeli, Finnland, Research Report 74: 101 P., 2007.
Beauvais et al. "Plasma Sprayed Biocompatible Coatings on PEEK Implants", Thermal Spray 2007: Global Coating Solutions, p. 371-376, 2007.
Ha et al. "Topographical Characterization and Microstructural Interface Analysis of Vacuum-Plasma-Sprayed Titanium and Hydroxyapatite Coatings on Carbon Fibre-Reinforced Poly(Etheretherketone)", Journal of Materials Science: Materials in Medicine, 8: 891-896, 1997.
Hargou et al. "Ultrasonic Activation of Mendable Polymer for Self-Healing Carbon-Epoxy Laminates", Composites: Part B, 45: 1031-1039, 2013.
Kim et al. "Detorque Force of TiN-Coated Abutment Screw With Various Coating Thickness After Repeated Closing and Opening", The Journal of Korean Academy of Prosthodontics, 45(6): 769-779, 2007.
Loy et al. "Lubrication of Polyether Ketone (PEEK) Surface by Liquid Ultrathin Films for High Wear Durability", WEAR, 296(1-2): 681-692, 2012.
Lugscheider et al. "Magnetron Sputtered Titanium Nitride Thin Films on Thermoplastic Polymers", Surface and Coatings Technology, 116-119: 1172-1178, 1999.
Simchi et al. "Recent Progress in Inorganic and Composite Coatings With Bactericidal Capability for Orthopaedic Applications", Nanomedicine: Nanotechnology, Biology, and Medicine, 7: 22-39, 2011.
Steinberg et al. "Carbon Fiber Reinforced Peek Optima—A Composite Material Biomechanical Properties and Wear/Debris Characteristics of CF-PEEK Composites for Orthopedic Trauma Implants", Journal of the Mechanical Behavior of Biomedical Materials, 17: 221-228, Jan. 2013.
Williams et al. "A Self-Healing Carbon Fibre Reinforced Polymer for Aerospace Applications", Composites: Part A, 38: 1525-1532, 2007.

* cited by examiner

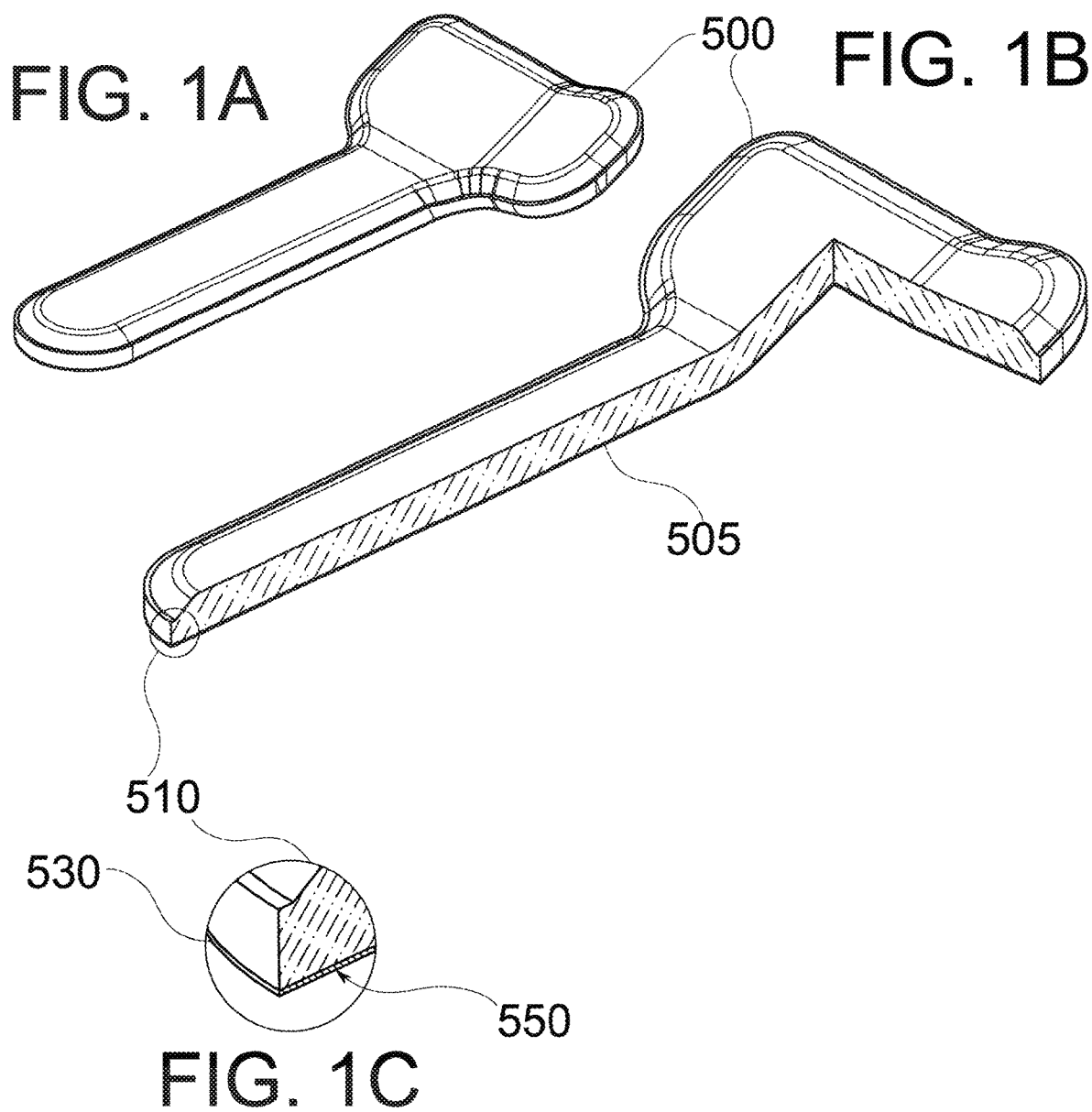

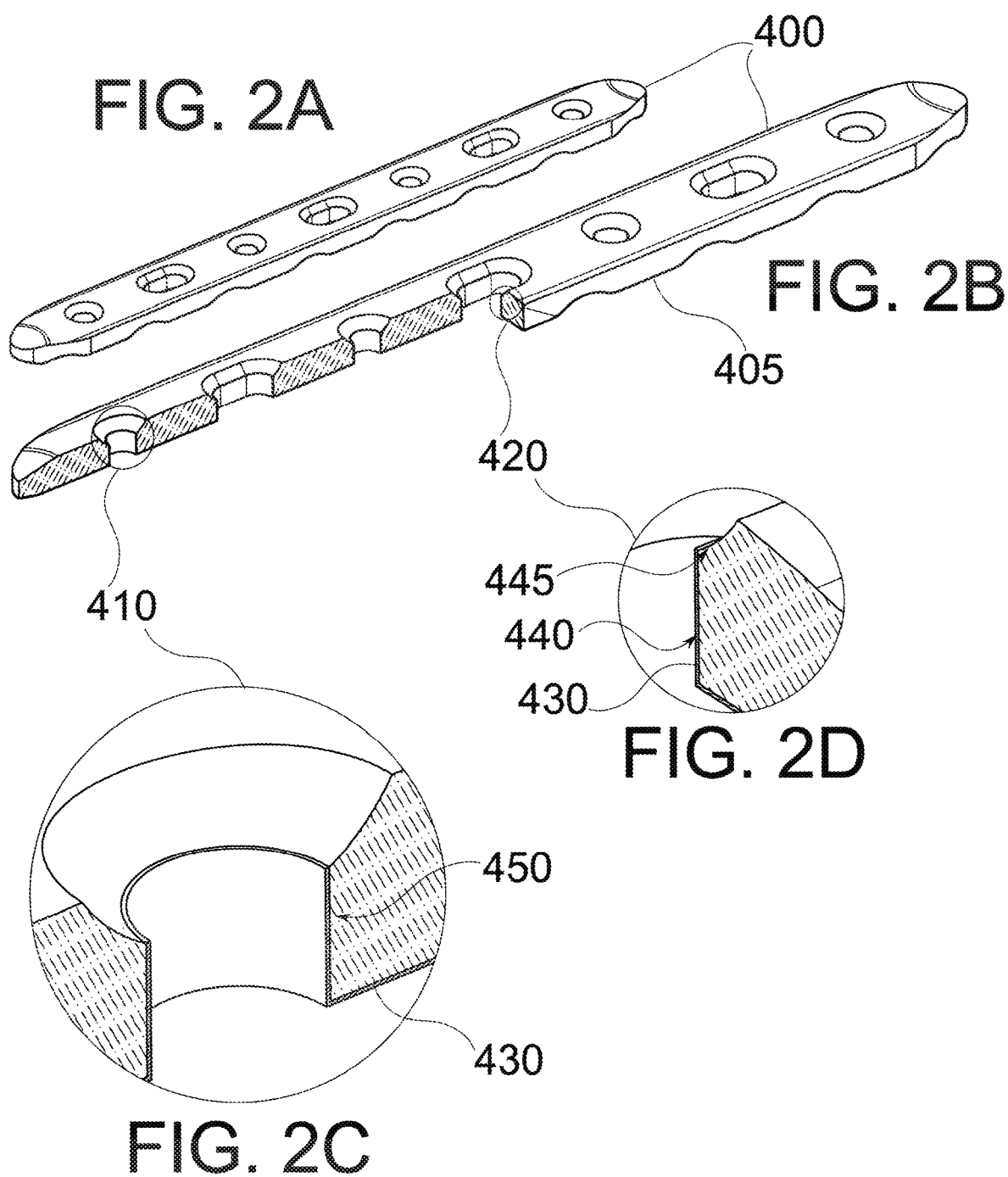

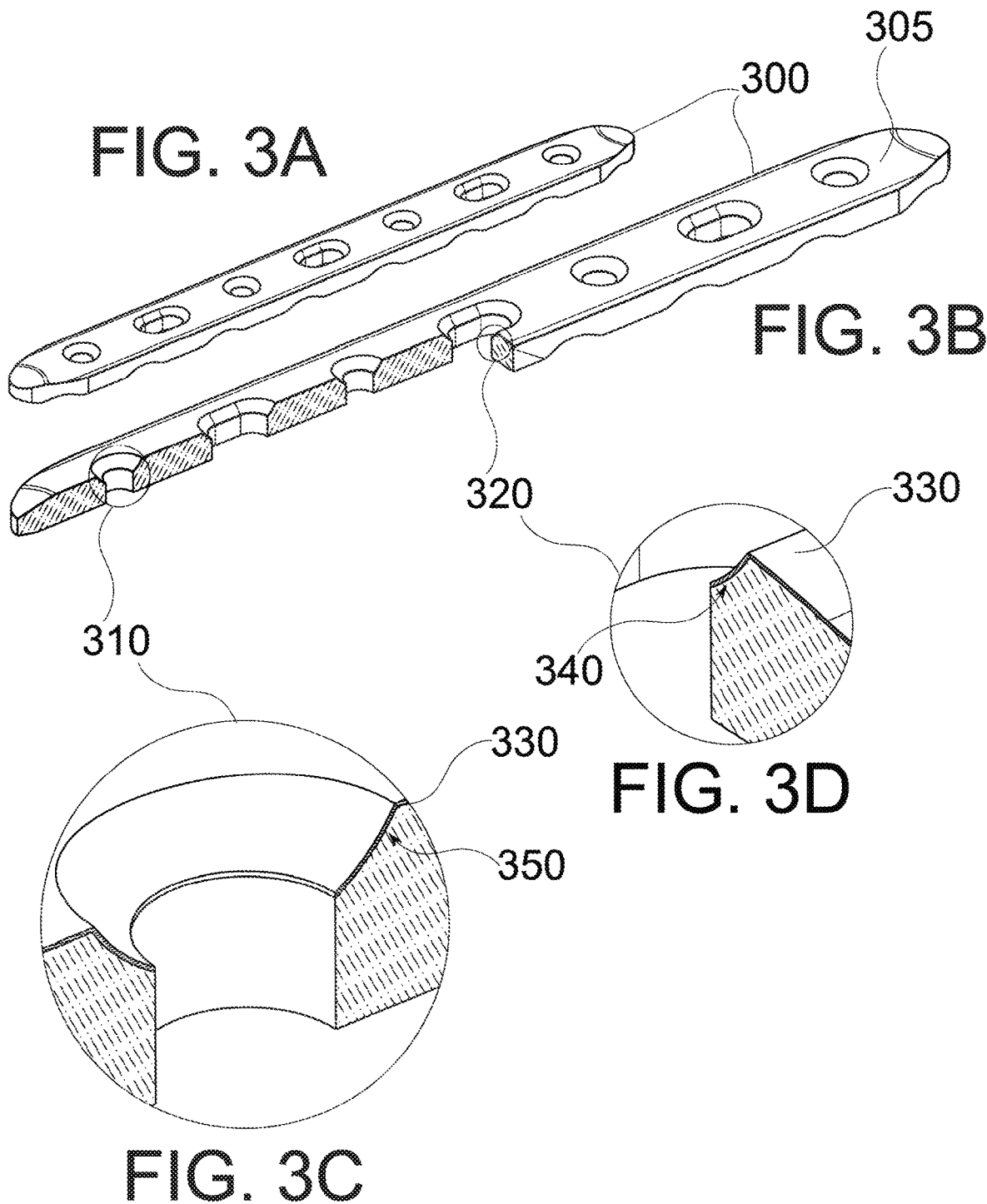

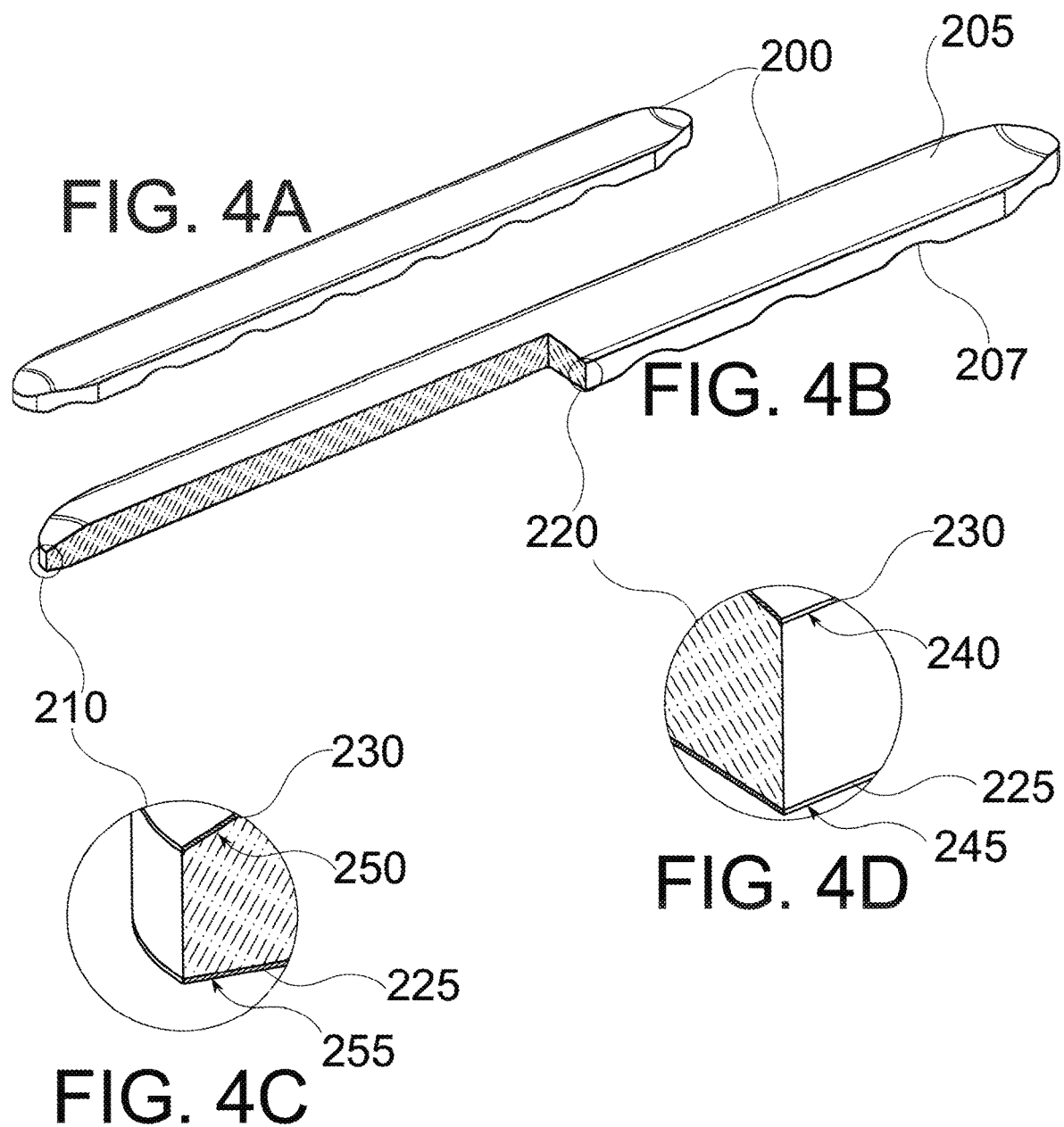

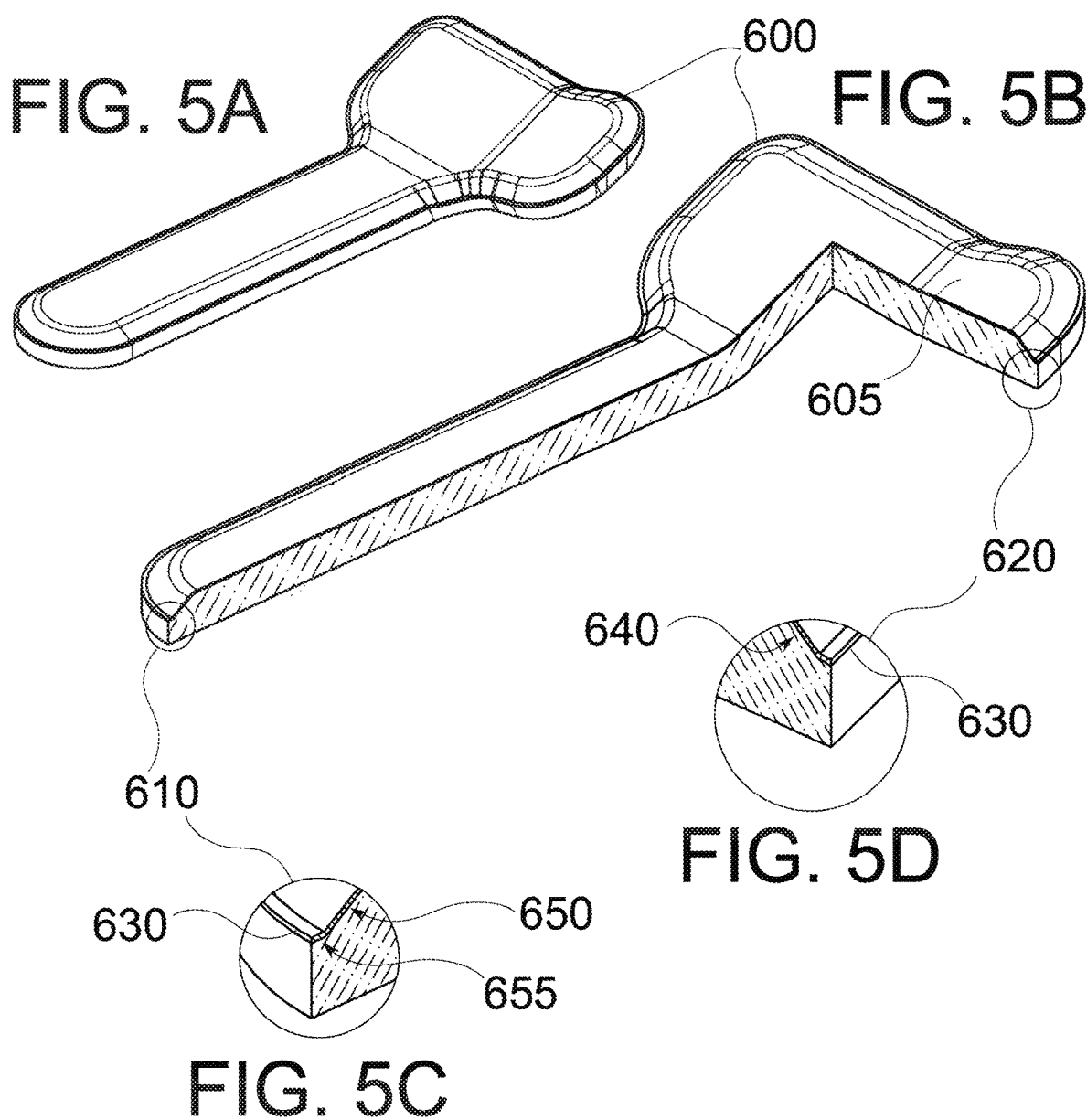

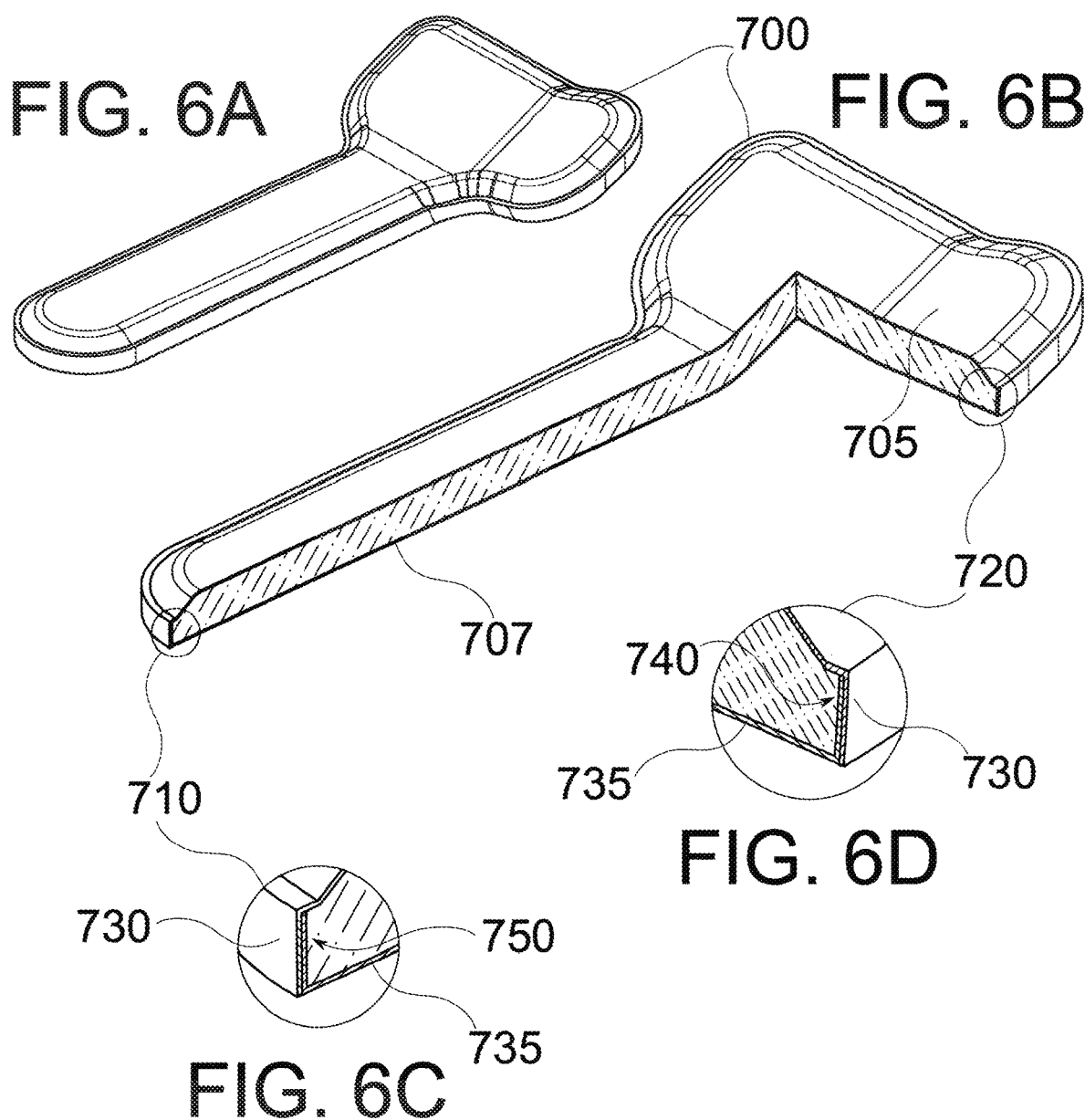

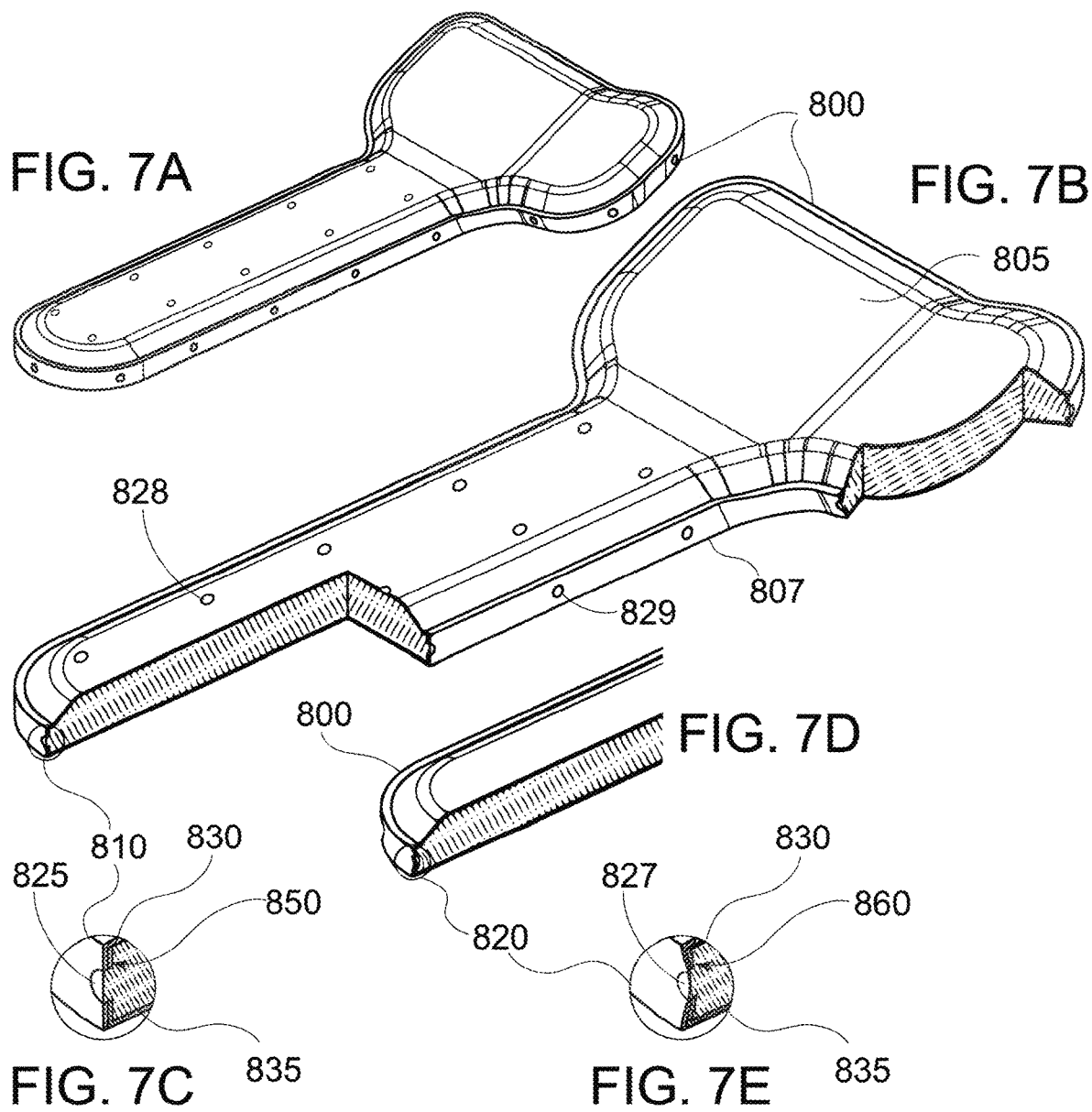

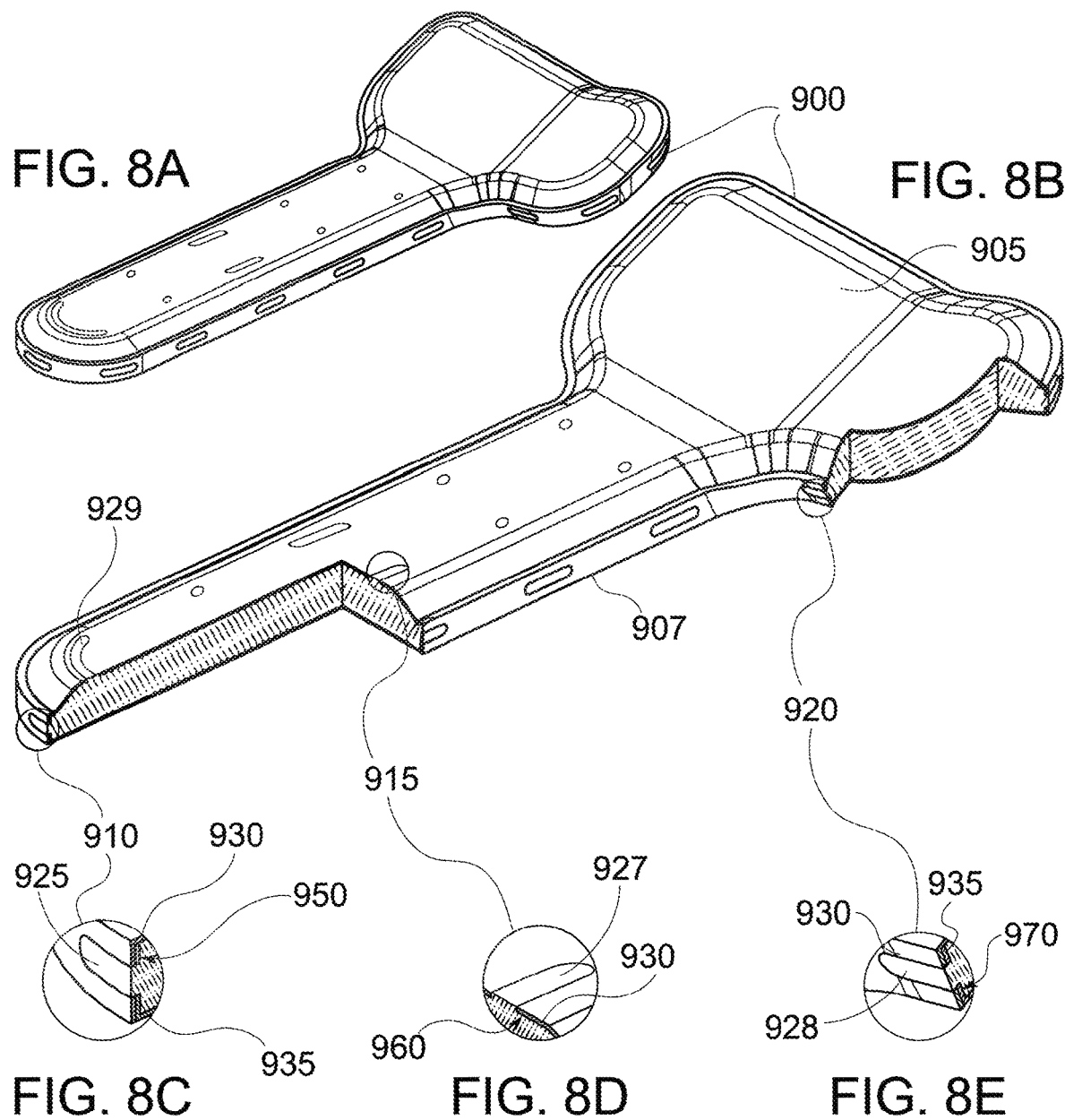

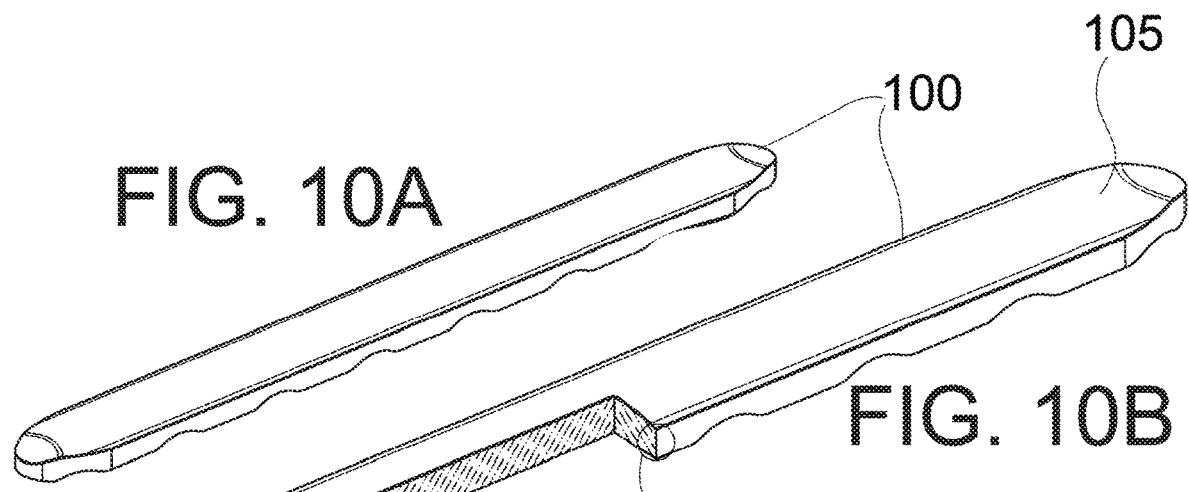
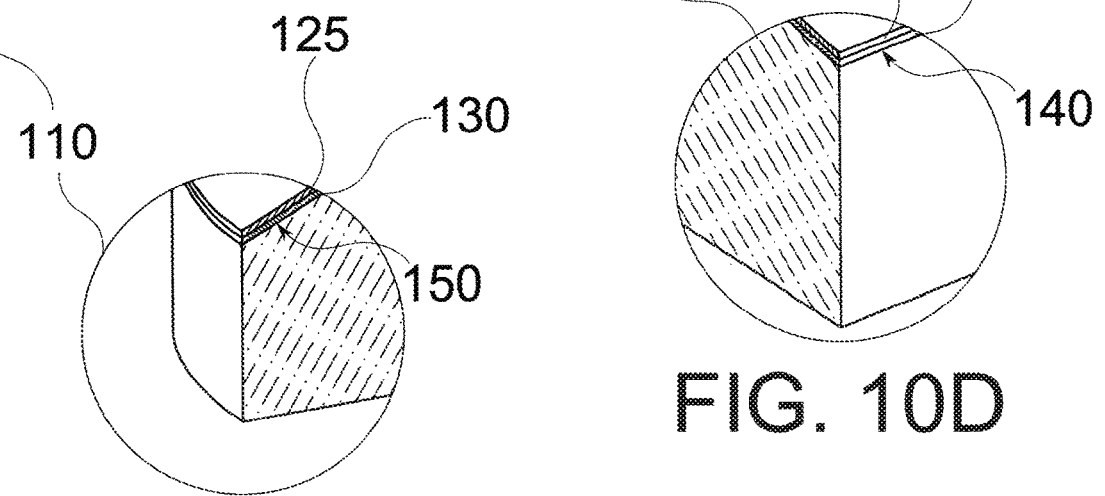

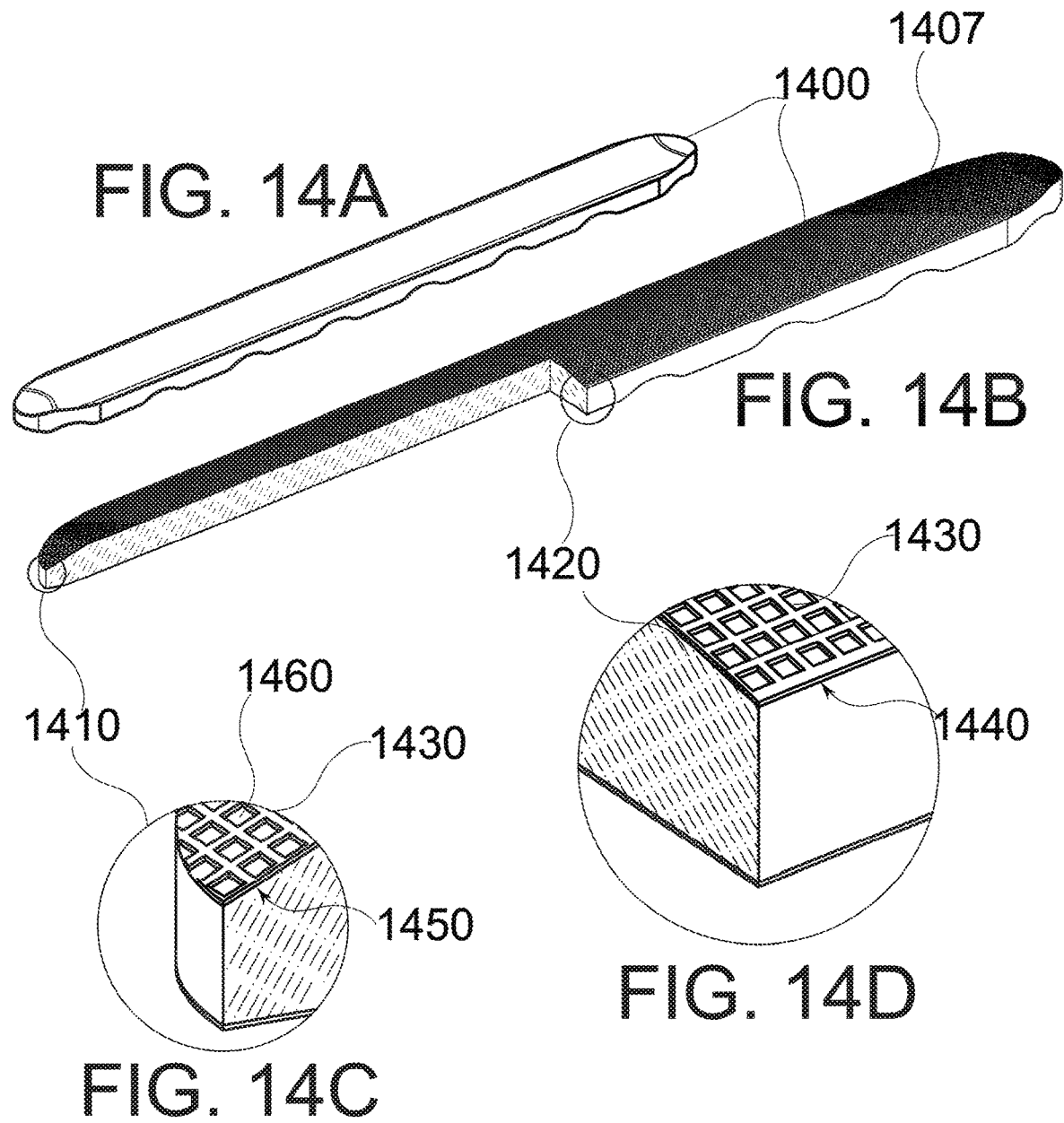

COMPOSITE IMPLANT COATING

RELATED APPLICATIONS

This application is a continuation of U.S. patent application Ser. No. 14/441,862 filed on May 11, 2015, which is a National Phase of PCT Patent Application No. PCT/IL2013/050927 having International Filing Date of Nov. 11, 2013, which claims the benefit of priority under 35 USC § 119(e) of U.S. Provisional Patent Application Nos. 61/841,966 filed on Jul. 2, 2013 and 61/724,983 filed Nov. 11, 2012.

The contents of the above applications are all incorporated by reference as if fully set forth herein in their entirety.

The present application is also related to International Patent Application No. PCT/IB2010/050225 to Beyar, filed on Jan. 18, 2010; to International Patent Application No. PCT/IB2011/052468 to Globerman, filed on Jun. 7, 2011; and to U.S. Provisional Patent Applications Nos. 61/586,853, 61/617,067 and 61/641,900, all to Beyar, filed on Jan. 16, 2012, Mar. 29, 2012, and May 30, 2012, respectively.

The contents of the above applications are all incorporated by reference as if fully set forth herein in their entirety.

FIELD AND BACKGROUND OF THE INVENTION

The present invention, in some embodiments thereof, relates to composite material bone implant devices and to manufacturing methods for such devices. More particularly, but not exclusively, the invention in some embodiments relates to such devices and methods as applied to implant devices formed of fiber-reinforced polymer matrices. Still more particularly, the invention in some embodiments relates to the surface characteristics of such implant devices, such as may be conferred, for example, by a surface coating.

Carbon fiber composite bone plates provide advantages in some properties over bone plates made of metal. A rigid metal bone plate creates relatively high stresses in certain regions of the bone, with insufficient load transfer, resulting in stress shielding. Both high stress and stress shielding can cause bone deterioration and resorption, leading to areas of bone weakness and loss of bone support for the implant.

Non-metal implants made of a lighter and more flexible material, yet having sufficient strength for load bearing, have been suggested in the past. In particular, composite material implants, for example formed of polymer reinforced with fibers, are discussed in U.S. Pat. No. 4,750,905; U.S. Pat. No. 5,181,930; U.S. Pat. No. 5,397,358, U.S. Pat. No. 5,009,664, U.S. Pat. No. 5,064,439, U.S. Pat. No. 4,978,360, and U.S. Pat. No. 7,419,714 the disclosures of which are incorporated herein by reference. Bone implants with coatings with properties affecting, for example, osteo-integration, bone regrowth, and biomimetic properties are discussed in European Patent Application EP19850304670, published as EP0169001; International Patent Application No. PCT/IB2004/003260, published as WO2006038056, International Patent Application No. PCT/CH2000/000382, published as WO2002004038; and European Patent Application EP20090702015, published as EP2245209.

The present invention addresses improvements in the above-noted areas, and in other areas of composite bone implant technology.

SUMMARY OF THE INVENTION

The present invention, in some embodiments thereof, relates to composite material bone implant devices and to manufacturing methods for such devices. More particularly, but not exclusively, the invention in some embodiments relates to such devices and methods as applied to implant devices formed of fiber-reinforced polymer matrices. Still more particularly, the invention in some embodiments relates to the surface characteristics of such implant devices, such as may be conferred, for example, by a surface coating.

According to an aspect of some embodiments of the present invention, including, for example, any of the embodiments described herein, there is provided a bone implant comprising: a body of fiber-reinforced polymer composite construction; and at least one layer of reinforcement fiber-free PEEK which shields said body from wearing contacts over at least one exterior facing surface region of said body.

According to some embodiments of the invention, including, for example, any of the embodiments described herein, the layer of reinforcement fiber-free PEEK comprises a layer molded to said body by compression molding.

According to some embodiments of the invention, for example, any of the embodiments described herein, the shielding comprises alteration of the appearance of particles shed from said bone implant.

According to an aspect of some embodiments of the present invention, for example, any of the embodiments described herein, there is provided an implantable bone plate comprising: a body of fiber-reinforced polymer composite construction; and at least one layer which shields the body from wearing contacts over at least one exterior facing surface region of the body.

According to some embodiments of the invention, for example, any of the embodiments described herein, the shielding is by interposition between the body and a wearing surface.

According to some embodiments of the invention, for example, any of the embodiments described herein, the wearing contacts comprise contacts with bone, and the coating is on a side of the implantable bone plate which contacts bone when the implantable bone plate is implanted.

According to some embodiments of the invention, for example, any of the embodiments described herein, the shielding is by conforming against the body.

According to some embodiments of the invention, for example, any of the embodiments described herein, the wearing contacts comprise contacts which would shed particles from the body.

According to some embodiments of the invention, for example, any of the embodiments described herein, the wearing contacts comprise contacts which would create fractures in the body.

According to some embodiments of the invention, for example, any of the embodiments described herein, the at least one layer conforms against the exterior-facing surface region.

According to some embodiments of the invention, for example, any of the embodiments described herein, the at least one layer conforms against all exterior-facing surface regions on one side of the body.

According to some embodiments of the invention, for example, any of the embodiments described herein, the at least one layer conforms against all exterior-facing surface regions of the body.

According to some embodiments of the invention, for example, any of the embodiments described herein, at least one edge region of the at least one layer is encased by material of the bone plate.

According to some embodiments of the invention, for example, any of the embodiments described herein, the material comprises a portion of the body.

According to some embodiments of the invention, for example, any of the embodiments described herein, the material comprises an extrusion of the body.

According to some embodiments of the invention, for example, any of the embodiments described herein, the extrusion comprises a shank and a head; the shank being attached at one end to the body, and the head being attached to the other end of the shank; the head being sized and positioned to interfere with the movement of the at least one layer relative to the body.

According to some embodiments of the invention, for example, any of the embodiments described herein, the extrusion is flanged.

According to some embodiments of the invention, for example, any of the embodiments described herein, the material comprises at least a portion of an at least second layer.

According to some embodiments of the invention, for example, any of the embodiments described herein, the at least second layer overlaps and conforms against at least a portion of the edge region.

According to some embodiments of the invention, for example, any of the embodiments described herein, the material comprises a restraining strip.

According to some embodiments of the invention, for example, any of the embodiments described herein, the restraining strip is bonded to the body.

According to some embodiments of the invention, for example, any of the embodiments described herein, the edge region of the layer is held within a recess of the body, the recess being at least partially filled by the restraining strip.

According to some embodiments of the invention, for example, any of the embodiments described herein, the edge region of the layer comprises a portion which is bent and within a recess of the body, the recess being at least partially filled by the restraining strip.

According to some embodiments of the invention, for example, any of the embodiments described herein, at least one region of the at least one layer is conformed against an interior-facing surface of the body.

According to some embodiments of the invention, for example, any of the embodiments described herein, the interior-facing surface is within a hole.

According to some embodiments of the invention, for example, any of the embodiments described herein, at least one region of the at least one layer is conformed against a chamfer of the body.

According to some embodiments of the invention, for example, any of the embodiments described herein, the chamfer is bounded on at least one side by a surface within a hole.

According to some embodiments of the invention, for example, any of the embodiments described herein, at least a portion of the body is conformed against an edge surface of the at least one layer.

According to some embodiments of the invention, for example, any of the embodiments described herein, the conformed portion comprises a pin.

According to some embodiments of the invention, for example, any of the embodiments described herein, the conformed portion attaches to a flange.

According to some embodiments of the invention, for example, any of the embodiments described herein, at least one edge surface of the at least one layer is conformed against a portion of the body.

According to some embodiments of the invention, for example, any of the embodiments described herein, at least a portion of the layer comprises a polymer material.

According to some embodiments of the invention, for example, any of the embodiments described herein, at least a portion of the layer is made of the matrix material component of the fiber-reinforced polymer composite.

According to some embodiments of the invention, for example, any of the embodiments described herein, at least a portion of the layer is made of PEEK.

According to some embodiments of the invention, for example, any of the embodiments described herein, at least a portion of the layer is made of metal.

According to some embodiments of the invention, for example, any of the embodiments described herein, at least a portion of the layer is made of titanium.

According to some embodiments of the invention, for example, any of the embodiments described herein, the at least one layer comprises at least two sublayers made of different materials.

According to some embodiments of the invention, for example, any of the embodiments described herein, the pin comprises an insertion which partially penetrates the material of the body.

According to an aspect of some embodiments of the present invention, for example, any of the embodiments described herein, there is provided a method for manufacturing an implantable bone implant comprising: forming a body of fiber-reinforced polymer composite construction, preparing at least one coating layer for the bone implant, and compression molding the bone implant together with the prepared at least one layer; such that the at least one coating layer is restrained against the surface of the body; and wherein the preparing comprises positioning the coating layer with respect to a surface of the body so that it shields the surface from wearing contacts.

According to some embodiments of the invention, for example, any of the embodiments described herein, the preparing comprises perforating the at least one coating layer.

According to some embodiments of the invention, for example, any of the embodiments described herein, the bone implant is a bone plate.

According to some embodiments of the invention, for example, any of the embodiments described herein, the bone implant is a bone screw.

According to an aspect of some embodiments of the present invention, for example, any of the embodiments described herein, there is provided an implantable bone plate comprising: a body of fiber-reinforced polymer composite construction; and at least one metal mesh structure integrated with the body.

According to some embodiments of the invention, for example, any of the embodiments described herein, the at least one metal mesh structure comprises a layer region conforming to a surface of the body.

According to some embodiments of the invention, for example, any of the embodiments described herein, the at least one metal mesh structure is at least partially embedded in the body.

According to some embodiments of the invention, for example, any of the embodiments described herein, the at least one metal mesh structure is comprised of titanium.

According to some embodiments of the invention, for example, any of the embodiments described herein, the at least one metal mesh structure is comprised of radio-opaque material.

According to some embodiments of the invention, for example, any of the embodiments described herein, the bone implant is a bone plate.

According to some embodiments of the invention, for example, any of the embodiments described herein, the bone implant is a bone screw.

According to some embodiments of the invention, for example, any of the embodiments described herein, the bone implant is a bone nail.

According to some embodiments of the invention, for example, any of the embodiments described herein, the coating layer comprises PEEK.

According to some embodiments of the invention, for example, any of the embodiments described herein, the coating layer comprises carbon fiber-free PEEK.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A schematically illustrates a perspective view of an exemplary coated bone plate coated on at least one surface, in accordance with some exemplary embodiments of the present invention;

FIGS. 1B-1C schematically illustrate perspective, sectional views of the bone plate of FIG. 1A in overview and/or in detail, in accordance with some exemplary embodiments of the present invention;

FIG. 2A schematically illustrates a perspective view of an exemplary coated bone plate coated on at least one hole-interior surface, in accordance with some exemplary embodiments of the present invention;

FIGS. 2B-2D schematically illustrate perspective, sectional views of the bone plate of FIG. 2A in overview and/or in detail, in accordance with some exemplary embodiments of the present invention;

FIG. 3A schematically illustrates a perspective view of an exemplary coated bone plate coated on at least one hole chamfer surface, in accordance with some exemplary embodiments of the present invention;

FIGS. 3B-3D schematically illustrate perspective, sectional views of the bone plate of FIG. 3A in overview and/or in detail, in accordance with some exemplary embodiments of the present invention;

FIG. 4A schematically illustrates a perspective view of an exemplary coated bone plate coated on at least two surfaces, in accordance with some exemplary embodiments of the present invention;

FIGS. 4B-4D schematically illustrate perspective, sectional views of the bone plate of FIG. 4A in overview and/or in detail, in accordance with some exemplary embodiments of the present invention;

FIG. 5A schematically illustrates a perspective view of an exemplary coated bone plate coated on at least one chamfer and/or rim surface, in accordance with some exemplary embodiments of the present invention;

FIGS. 5B-5D schematically illustrate perspective, sectional views of the bone plate of FIG. 5A in overview and/or in detail, in accordance with some exemplary embodiments of the present invention;

FIG. 6A schematically illustrates a perspective view of an exemplary coated bone plate coated on at least two surfaces and having at least one region where coating layers overlap, in accordance with some exemplary embodiments of the present invention;

FIGS. 6B-6D schematically illustrate perspective, sectional views of the bone plate of FIG. 6A in overview and/or in detail, in accordance with some exemplary embodiments of the present invention;

FIG. 7A schematically illustrates a perspective view of an exemplary coated bone plate coated on at least one surface and having at least one region where a coating layer is held in place by a pin formation, in accordance with some exemplary embodiments of the present invention;

FIGS. 7B-7E schematically illustrate perspective, sectional views of the bone plate of FIG. 7A in overview and/or in detail, in accordance with some exemplary embodiments of the present invention;

FIG. 8A schematically illustrates a perspective view of an exemplary coated bone plate coated on at least one surface and having at least one region where a coating layer is held in place by an elongated pin formation, in accordance with some exemplary embodiments of the present invention;

FIGS. 8B-8E schematically illustrate perspective, sectional views of the bone plate of FIG. 8A in overview and/or in detail, in accordance with some exemplary embodiments of the present invention;

FIG. 10A schematically illustrates a perspective view of an exemplary coated bone plate coated on at least one surface by at least two coating layers, in accordance with some exemplary embodiments of the present invention;

FIGS. 10B-10D schematically illustrate perspective, sectional views of the bone plate of FIG. 10A in overview and/or in detail, in accordance with some exemplary embodiments of the present invention;

FIGS. 14A-14D schematically illustrate perspective views in whole, sectionally, and/or in detail of an exemplary coated bone plate having an aperture-patterned layer on at least one surface, in accordance with some exemplary embodiments of the present invention;

DESCRIPTION OF SPECIFIC EMBODIMENTS OF THE INVENTION

Figure 9A:
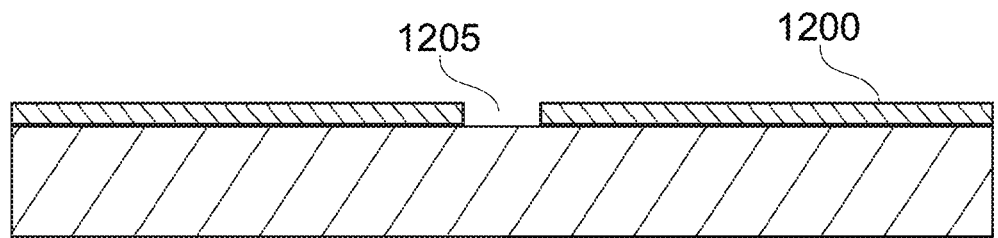
FIGS. 9A-9C schematically illustrate sectional views of phases in the extrusive formation of a retaining structure for restraining a coating layer to the body of a bone plate implant, in accordance with some exemplary embodiments of the present invention.

The present invention, in some embodiments thereof, relates to composite material bone implant devices and to manufacturing methods for such devices. More particularly, but not exclusively, the invention in some embodiments relates to such devices and methods as applied to implant devices formed of fiber-reinforced polymer matrices. Still more particularly, the invention in some embodiments relates to the surface characteristics of such implant devices, such as may be conferred, for example, by a surface coating.

Overview

An aspect of some embodiments of the invention relates to a coating layer which shields a portion of a bone implant surface from wearing interactions with bone and/or with other bone implant component surfaces. In some embodiments of the invention, the coating layer comprises a polymer, for example PEEK. In some embodiments of the invention, the coating layer is of a metal foil, such as titanium.

According to some embodiments, other coating materials are used, for example, as described hereinbelow. In some embodiments of the invention, the coated bone implant is a bone plate, a bone screw, and/or a bone nail.

A potential advantage of such a coating is to prevent the shedding of particles from an implant. Shed particles may be difficult to distinguish from evidence of potentially dangerous conditions, for example, microorganism contamination and/or degenerating tissue. A coating may also provide an advantage with respect to inspection and/or aesthetics. There may be a particular potential advantage in one or more of these respects when shed particles are dark.

An aspect of some embodiments of the invention relates to a polymer coating layer (for example, PEEK or PEKK) for a bone implant having a composite, fiber-reinforced body, wherein the polymer coating is substantially free of reinforcing fibers of the type used in the implant body. In some embodiments, substantially free means having <10% of the reinforcing fiber content of the implant body, <5%, <1%, <0.5%, <0.1%, or less than an intermediate, greater or lesser threshold of relative reinforcing fiber concentration. In some embodiments the polymer coating is entirely free of reinforcing fibers. Optionally, the polymer coating contains fibers of a different composition than the reinforcing fibers of the implant body. In some embodiments, the coating layer polymer is comprised of material of a composition matching the material of the composite material matrix.

An aspect of some embodiments of the invention relates to a plurality of layers for the coating. In some embodiments, coatings are overlaid over all or a portion of their extent, with each layer potentially providing specific properties to the bone implant according to its construction and composition. In some embodiments, coatings are provided with construction and composition determined differently for different regions of the bone implant; for example, differently for a top- and for a bone-facing surface, or differently for a hole- and non-hole-surface. Non-hole surfaces in general, and top-facing, bone-facing, and outer-side facing surfaces in particular are exterior surfaces of the bone implant. In some embodiments, one or more regions of overlap between layers contribute to the attachment of at least one of the layers to the bone implant.

An aspect of some embodiments of the invention relates to radio-opaque elements which are embedded in, overlie and/or underlie a coating. Optionally, the radio-opaque elements are arranged in an encoding configuration. Radio-opaque elements may provide an advantage for determining orientation and/or identification of a bone implant from a radiographic image.

An aspect of some embodiments of the invention relates to grouped apertures in layer structures of a bone plate implant. In some embodiments, grouped apertures exist within, for example, a mesh, grid, screen, grating, weave, and/or wire winding.

In some embodiments, grouped apertures are collectively comprised in a region of relative transparency to one or more imaging modalities, for example, MRI, X-ray, CT, and/or visible light. In some embodiments, apertures are holes in a layer of material. In some embodiments, apertures are defined as such according to transparency or relative transparency in an imaging modality (for example, in the sense that a glazed window pane is an aperture for visible light). In particular, relative thinness of a region potentially creates an aperture for imaging through. In some embodiments, the mesh (apertured) structure is made of metal. In some embodiments, the mesh structure is a coating and/or an undercoating. In some embodiments, the mesh structure is integrated into the bulk structure of the bone implant. In some embodiments, the material forming the mesh structure is radio-opaque relative to the bulk structure of the bone plate implant.

An aspect of some embodiments of the invention relates more generally to composite material bone plate implants coated with material which differs from the bulk material composition of the implant. Such a coating may confer a desired property to the implant.

An aspect of some embodiments of the invention relates to processes, methods, and/or structural features used to secure a coating to a composite material bone plate implant. A coating may be secured, for example, by adhesion or bonding; and/or secured by geometrical restraint and/or frictional forces. A coating may be made to conform to the surface of an underlying bone implant in different ways: for example, by being initially created on the implant surface (for example, by spraying or dip-coating), or by being separately created and then pressed onto the implant surface (for example, by compression molding). A conforming coating generally follows the bulk outlines of the underlying bone implant. In some embodiments, coatings also conform with bone implant structures such as chamfers and/or holes. In some embodiments, a conforming coating has shape details which diverge from the underlying implant body. In some embodiments, this occurs, for example, at points where implant body and coating layer interact (including at restraining pins or strips), to provide shape-locking attachment, or where two or more coating layers are shaped around one another, as herein described.

An aspect of some embodiments of the invention relates to pin formations which comprise a shank that fits into an aperture of the coating layer and attaches to and/or is continuous with the material of the bone plate implant underneath. In some embodiments, the shank is topped by a cap which interferes with the removal of a coating layer.

An aspect of some embodiments of the invention relates to the surface appearance of the implant. In some embodiments, a coating is provided which changes the surface appearance to meet an aesthetic requirement, for example, a positive aesthetic requirement such as a need to present the appearance of a metallic surface, or a negative requirement, such as the need to present a surface which is not black.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Bone Wear Shielding

Reference is now made to FIGS. 1A-1C which schematically illustrate perspective views in whole or sectionally, and/or in detail 510, of exemplary coated bone plate implant 500 coated on at least one surface 505, 550, in accordance with some exemplary embodiments of the present invention. The example of FIG. 1A illustrates a form like that of a distal radius plate such as may be used in wrist fracture repair treatments.

In some embodiments of the invention, a coating surface with an increased hardness, fracture toughness, and/or decreased coefficient of friction with respect to the uncoated surface of the bone implant is selected. There is a potential advantage achievable thereby in reducing the number of particles shed. This potential advantage applies even when the bulk material of a bone plate implant is mechanically sufficient for uncoated use in a bone implant, even in contact with wearing surfaces such as bone. A surface with increased fracture toughness with respect to the uncoated bone implant surface provides a potential advantage by reducing the occurrence of fractures which spread to the body of the implant and undermine structural integrity.

It should be noted that the surfaces of a bone plate implant are commonly exposed to different environments during and after implantation. In particular, in some embodiments of bone implants having two surfaces of greatest extent (for example, surfaces 705 and 707 of FIG. 6B) one side (for example, 707, the "bone" or "bottom" side of the implant) is installed against bone, while the other ("top" side 705) contacts soft tissue. Bone contact is a particular source of contact wear on a bone implant.

In some embodiments of the invention a surface is modified so that particles it does shed are distinctive and/or preferred in size and/or appearance. For example, the surface is chosen to present a metallic, transparent, or some clearly artificial coloration and/or appearance. In some embodiments, the surface is chosen to present a textured and/or patterned appearance. Particles shed from a bone implant surface due to normal wearing interactions may not be readily distinguishable from evidence of potentially dangerous conditions, for example, microorganism contamination and/or degenerating tissue. Carbon fibers, for example, contribute to shed particles a dark (gray or black) coloration which may appear pathological. In some embodiments, a surface is modified so that shed particles are of a predetermined size range. Optionally, the size range is selected for its biocompatibility; for example, a larger particle size range may be more biocompatible than a size range comprising nanoparticles smaller than a micron, smaller than 0.5 micron, or smaller than 0.1 microns.

A potential advantage is provided by a surface which sheds particles that are clearly distinguishable from evidence of a dangerous condition, and/or which sheds fewer particles. Shedding of few particles may be an advantage, for example, to reduce staining of surrounding tissue, and/or to make inspection of an implant site easier.

In some exemplary embodiments of the invention, a bone plate implant 500 is coated by coating layer 530 over a surface 505 or portion of a surface 550 which, when implanted, is in contact with hard material, such as bone, over at least a portion of its extent.

It is potentially advantageous to provide a surface material chosen for a potentially enhanced wear durability compared to the native surface of a bone plate implant. In some embodiments, the material of coating layer 530 of a bone plate implant 500 is chosen to potentially provide high surface hardness and/or fracture toughness to the implant. The hardness is chosen, for example to be greater than 20 HRC, greater than 25 HRC, or greater than 30 HRC. ATI Ti-6Al-4V, for example, has a hardness greater than 30 HRC. A chosen fracture toughness for a coating material is for example, greater than 1 MPa·m$^{1/2}$, greater than 2 MPa·m$^{1/2}$, or greater than 5 MPa·m$^{1/2}$. In some embodiments, the implant is coated with one of the following materials: titanium (Ti), titanium nitride (TiN) (Lugscheider, 1999; Kim, 2007), titanium aluminum nitride Ti—Al—N), another titanium ceramic or alloy, diamond like carbon (DLC), another ceramic or metal material, or another suitable material. Such materials provide the potential advantage of conferring surface hardness that improves, for example, on the hardness of a composite material surface of carbon fiber in PEEK. This may in turn provide an advantage by reducing particle shedding due to contacts with bone.

In some exemplary embodiments, the coating layer 530 of a bone plate implant is chosen to potentially reduce a coefficient of friction. A reduced coefficient of friction may provide an advantage for wear durability. Such a coating is described, for example, by Zheng (2012). A DLC film may also provide a lowered coefficient of friction. In some embodiments, a friction reducing layer is added over a layer of material selected for hardness and/or toughness.

In some embodiments, the debris-shedding properties of a bone plate implant surface 505 are changed, for example, by coating the implant with a material which does not shed particles that may be confused with evidence of a dangerous condition.

In some embodiments, this is the material of the composite matrix. Optionally, for example, a PEEK-carbon fiber composite material is coated with PEEK.

Optionally, another material with desirable appearance characteristics is chosen. This may provide an advantage, for example, by modifying the nature of shed particles so that they are clearly distinct from evidence of a dangerous condition. Such an advantage is obtainable even if the net number of particles shed is not affected, or increased.

In some exemplary embodiments, the coating layer 530 of a bone plate implant is chosen to affect the bioreactivity of the surface. In some embodiments, the material is chosen to promote osteo-integration. Such a material may be, for example, titanium oxide or hydroxyapetite.

Exemplary Manufacturing Methods

A coating may be provided according to one or more of a selection of manufacturing techniques. In some embodiments corresponding to bone plate implant 500, and to other coated bone implants herein described, coating is performed using compression molding.

In some embodiments corresponding to bone plate implant 500, and other coated bone implant embodiments as herein described, coating is by other methods, alone or in combination. In some embodiments, for example, physical vapor deposition (PVD) (Rahamathunnisa, 2007) is used. Optionally, PVD follows preparation of the surface of the implant; for example, by grid blast, bombardment of argon ionized ions, or other surface treatment. In some embodiments, the coating is added using a vacuum plasma spray (VPS) technique, optionally following preparation of the surface of the implant (Ha, 1997; Beauvais).

Other contemplated methods for application of a coating include dip-coating, spray-coating, chemical vapor deposition, etching, surface polymerization, electrochemical deposition, electroplating and 3D printing. Other contemplated forms of application include, for example as film, particles, vapor, and/or as solution. Examples of the material composition of a coating include metals, polymers, ceramics and composites.

Compression Molding for Bone Plate Implant Surfacing

According to an aspect of some exemplary embodiments of the invention, a bone plate implant 500 is coated with at least one separately prepared layer that is attached to the bone plate implant. A separately prepared layer may be, for example, a metal foil, a polymer film, a polymer tape, and/or another material which is rendered into a flat form susceptible of layering onto a surface. In some embodiments of the invention, the attachment is by adhesion, for example using an adhesive, or for example by preparing surfaces so that they adhere after undergoing a manufacturing step such as compression molding. In some embodiments, attachment is mechanical, for example, due to restraining interactions between the implant body and one or more layers, between layers, or between some combination of layers and implant body. Layers may be physically and/or chemically integrated into the body of the implant during manufacturing. In some embodiments, layer attachment is established using compression molding. A potential advantage of compression molding is to allow bonding and/or mechanical restraint of coating layers to a bone plate implant surface, depending on the specifics of material, geometry, and coating method.

In some embodiments, a coating layer 530 is molded along with the main body of the bone plate implant 500. In some embodiments, the surface of an already shaped bone plate implant 500 is modified via a secondary compression molding step.

In some embodiments, the surface is modified via a tertiary or greater compression molding step. In some embodiments, another coating method, for example one of those listed above, is used to apply at least a first coat to a bone plate implant 500 before or after a compression molding step which applies and/or establishes the attachment of a further surface treatment such as an additional layer of material.

In some embodiments, material is layered over at least one region of the implant 505, 550 to form a coating layer 530. In some embodiments, layered material is in the form of a metal foil; for example, titanium, titanium alloy, or another metal.

Alternatively or additionally, layered material is in the form of tape; for example, a tape of PEEK, PEKK or another polymer. According to the embodiment, the at least one region is, for example: all implant surfaces, one or more sides and/or portions thereof, and/or all or portions of one or more interior surfaces. In some embodiments, the portion of the surface covered by a coating layer is 10%, 20%, 50%, 80%, 100%, or another intermediate fraction of the total surface. In some embodiments, the portion covered is continuous. In some embodiments, the portion covered is discontinuous.

According to the embodiment, the layered thickness of foil, polymer, and/or other coating materials, before and/or after compression, ranges between, for example: between 100 nanometers and 1 micron, between 1 micron and 10 microns, between 10 microns and 100 microns, between 100 microns and 1 mm, and between 1 mm and 2 mm. In some embodiments, a different thickness is applied at different regions of the implant. If a material is to be on an exposed surface, it is chosen to be biocompatible (potentially comprising, for example, biocompatible polymers, metal alloys comprising titanium, nickel-titanium, stainless steel, and/or another material such as hydroxylapatite). Optionally, if buried under more superficial layers, materials which are not biocompatible are used.

The wrapped composite is put under pressure; for example, a pressure higher than 50 atm, 100 atm, 400 atm, 700 atm, or 1000 atm. In some embodiments, the pressure used is between 100 atm and 150 atm. Optionally, the temperature is selected so that compression molding induces integration between the outer layer and the matrix below; for example, between 380° C., 400° C., 405° C. or 410° C. In some embodiments, the tolerance range on the temperature is ±1° C., ±2° C., ±5° C., or ±10° C.

Optionally, the temperature is selected to be slightly above the polymer melting point. Optionally, the temperature and/or molding pressure is selected so that compression molding causes at least partial flow of one or more of the applied layer materials.

In some embodiments, material layers of potentially different material composition are added as a surface modification coating to be formed in the same compression molding step. This is further discussed herein in relation to FIGS. 10A-10D. Optionally, the material is added in the form of tapes. Relative to the implant overall length or overall width, the tape width may be, for example, 1%, 5%, 10%, 50%, or 100% or more of the implant's size. In some embodiments, tapes are self-overlapping. According to the embodiment, tape is wound around any axis of the bone implant. Optionally, different lengths of tape are wound in different directions.

Optionally, material layers are applied separately and molded in at least two compression molding steps. Optionally, material layers are placed in a predetermined order, chosen according to their properties, to produce a bone implant of predetermined properties. Optionally, the predetermined order varies at different locations on and/or within the implant. Optionally, material layers are placed with predetermined, and potentially different orientations.

More specifics of compression molding use in manufacturing coatings for bone plate implants are discussed herein, in connection with the drawings.

Coating Holes

Reference is now made to FIGS. 2A-2D which schematically illustrate perspective views in whole or sectionally, and/or in detail 410, 420 of exemplary coated bone plate 400 coated on at least one hole interior surface 440, 450, in accordance with some exemplary embodiments of the present invention. The example of FIG. 2A illustrates a form like that of a diaphyseal plate such as may be used in long bone repair treatments.

Wearing interactions upon surfaces of a bone plate implant may occur with other implant components, for example, screws. In some embodiments of the invention, a coating layer is provided which intrudes into holes. A potential advantage of a coating which enters a hole is to provide anchoring for the coating layer; for example by adherence and/or by shape-locking.

In some exemplary embodiments of the invention, a bone plate implant 400 is coated by coating layer 430 which intrudes into a hole and covers at least a portion of an interior hole surface, 440, 450. Optionally, coating layer 430 is contiguous with portions of a coating layer covering another surface 405, which, when implanted, is in contact with bone. In some embodiments, coating layer 430 may include a region 445 which extends to cover at least a portion of a partially interior hole surface, such as a chamfer. In some embodiments, the covered height of the chamfer around a whole or partial circumference is at least 20%, at least 30%, at least 50%, or 100% of the overall height of the chamfer. In some embodiments, the circumferential portion of the chamfer which is covered is at least 20%, at least 30%, at least 50%, or 100% of the full circumference of the chamfer.

In some embodiments of the invention, the coating material is ductile so that it conforms to the hole aperture during pressure molding. In some embodiments, a whole or partial insert sleeve is provided which conforms to the hole aperture, and/or is made to conform by pressure molding. In some embodiments, coating material is cut before being applied to bone plate implant 400 so that a flap of it inserts into the hole and is pressed against a portion of the interior hole surface, for example, during pressure molding. In some embodiments, two or more such flaps insert into the hole.

In some embodiments, the interior surface of one or more coated holes is smooth. In some embodiments, the interior surface of one or more coated holes is threaded.

It should be noted that the presence of holes and the use of hole coatings described herein is not confined to embodiments having the shape of bone plate implant 400. For example, some embodiments shaped like bone plate 500, or with another shape suitable for a bone plate, are manufactured with holes. In some embodiments, at least one of these holes is at least partially coated.

In some embodiments of the invention, compression molding during manufacture forces a plastic layer material, for example a foil or a polymer tape, to conform to at least a portion of the interior surface 440, 450 of one or more holes in a bone plate implant 400. This may provide advantages over coating techniques for which a hole region is inaccessible or difficult to coat. It may provide advantages over the use of pre-formed hole inserts, for example, by reducing the complexity of manufacture.

In some embodiments, the form assumed by a coating layer may itself serve to restrain the coating upon the body of the bone implant. For example, a foil coating may insert into, curve around, and/or wrap around a portion of the implant, restricting the directions in which the coating may move relative to the bone implant body without further deformation. In some embodiments, shape locking prevents relative motion altogether. Such shape locking is a potential advantage of applying a coating layer with at least partial hole penetration.

Reference is now made to FIGS. 3A-3D which schematically illustrate perspective views in whole or sectionally, and/or in detail 310, 320, of exemplary coated bone plate 300 coated on at least one hole chamfer surface 340, 350, in accordance with some exemplary embodiments of the present invention.

In some embodiments, a hole is coated throughout its extent. A potential advantage of this is to ensure complete protection of hole surfaces exposed to wearing interactions. Another potential advantage is to provide shape-locking.

In some exemplary embodiments of the invention, a bone plate implant 300 is coated by coating layer 330 which intrudes into a hole region so as to coat at least a portion of a chamfer and/or an interior hole surface, 340, 350. In some embodiments, the covered height of the chamfer around a whole or partial circumference is at least 20%, at least 30%, at least 50%, or 100% of the overall height of the chamfer. In some embodiments, the circumferential portion of the chamfer which is covered is at least 20%, at least 30%, at least 50%, or 100% of the full circumference of the chamfer. Optionally, coating layer 330 is contiguous with portions of a coating layer covering another surface 305.

In some embodiments of the invention, fully coated holes are produced by a combination of the coated embodiment of bone plate implant 300 with the coated embodiment of bone plate implant 400. Optionally, such an embodiment is produced in one or in separate compression molding steps. Optionally, layers from entering the hole from opposing sides overlap one another. In some embodiments, a portion of the layer which enters the hole is made thicker; for example, so as to provide additional protection for regions which are contacted by the threads of a screw.

Examples of coatings comprising two or more surfaces are discussed in more detail in connection with other embodiments described herein.

Coating of Multiple Surfaces

Reference is now made to FIGS. 4A-4D which schematically illustrate perspective views in whole or sectionally, and/or in detail 210, 220, of exemplary coated bone plate 200 coated on at least two surfaces 205, 207, in accordance with some exemplary embodiments of the present invention.

According to some exemplary embodiments of the invention, a bone plate implant is coated on surfaces additional or alternative to those which are liable to wearing interactions with hard surfaces, such as bone.

Apart from debris produced by wearing interactions, there are potential drawbacks to the normal visual appearance of some bone plate implant surfaces, such as surfaces of carbon fiber composite. Coloration may interfere with inspection of the implant for flaws such as cracks or contamination.

Coloration may alter the visual contrast of the implant with surrounding implant elements and/or tissue.

Aesthetically, a surface with unusual coloration compared to other bone implant materials may be distracting and/or disturbing. Carbon fibers tend to darken composites of which they are a part, potentially contributing to one or more of these drawbacks.

There are also potential advantages to using color as an indicator. In some embodiments, for example, a coating color is chosen so that it is clearly distinct from endogenous colors. This may provide an advantage, for example, by helping to ensure that shed particles are not mistaken for signs of infection and/or tissue damage. In some embodiments, layers of different colors are provided, potentially serving as an indicator of bone implant wear.

In some exemplary embodiments of the invention, a bone plate implant 200 is coated by coating layer 225, 230 over a surface 205, 207 or portion of a surface 240, 245, 250, 255. The material of coating layer 225 and coating layer 230 may be the same, or different. Optionally, the coating material is chosen from among those discussed in connection to other embodiments of the invention; for example, to provide wear durability or for appearance. In some cases, the coating material is chosen from among those next discussed in connection with other surface properties.

Other Surface Properties

According to an aspect of some embodiments of the present invention, determination of the surface properties of a bone plate implant conferred by a coating is not limited to considerations of wear characteristics or appearance. Conferred properties may relate to, for example, self-healing, and/or biological activity.

Self-Healing

According to an aspect of some embodiments of the present invention, material properties and/or the process of manufacturing and/or a process of post-manufacturing treatment is chosen or designed to introduce one or more self-healing properties into a bone plate implant. A self-healing property is one that, when activated, initiates a change that tends to prevent the implant from failing to function within its intended physical, chemical and/or biological specifications.

During manufacturing of some embodiments of the invention, one or more self-healing agents is added at one or more predetermined locations on or within the bone implant. Optionally, a self-healing agent is added in a predetermined amount and/or concentration. Optionally, a self-healing agent is added alone. Optionally, a self-healing agent is added in a formulation. Optionally, an encapsulated agent is formulated within an inert outer shell. Optionally, a self-healing agent comprises a combination of compounds which perform their healing effect when mixed.

In some embodiments, the operation of a self-healing agent in a bone implant is triggered by a change in the implant material with respect to original specifications.

The action of self-healing can be initiated with and without an external trigger. Exemplifying the former, Hargou (2012), describes ultrasonic activation of self-healing in carbon-epoxy laminates. Exemplifying the latter, Williams (2007) describes a self-healing agent (Cytec Cycom 823) encapsulated within microparticles embedded in carbon reinforced composite. When a crack begins to propagate, the sealing agent leaches from the particle. This tends to close the crack and prevent further propagation.

In an exemplary embodiment of the invention, foils and/or polymer tapes (such as PEEK or PEKK or others), at least one of which contains a self-healing agent, are layered upon the bone implant. Such a self-healing agent may act, for example, to help seal propagating cracks originating near the surface of implant due to long-term cyclic loads in vivo. Optionally, layers are added in a predetermined order. Optionally, layers are added with a specific orientation, for example to determine directions in which greatest strength is added. Optionally, layer structure varies according to position on the implant, possibly with respect, for example, to layer number, layer thickness, layer orientation, and/or layer materials. In some embodiments of the invention, compression molding is performed under conditions of pressure and temperature which do not damage the activity of the self-healing agent.

Biological Activity

In some exemplary embodiments, the coating of a bone plate implant is chosen to determine the osteo-conductive and/or osteo-inductive properties of the implant. Coatings which may improve such properties include, for example, porous titanium or hydroxyapatite (HA). In some embodiments of the invention, the coating is separable from the underlying bone implant. A potential advantage of such a separation is to allow an osteo-integrated bone implant to be removed from an implant site with lowered disruption to regrown bone material.

In some exemplary embodiments, the coating of a bone plate implant is chosen to potentially reduce a bacterial burden. Optionally, the outer layer is chosen with particular attention to its smoothness, such as a smooth PEEK tape. Smoother PEEK surfaces may carry a lower bacterial load relative to similar samples having a rougher surface (Rochford, 2010).

In some exemplary embodiments, the coating of a bone plate implant presents and/or releases to the surrounding tissue a pharmaceutically active material, for example, one with anti-inflammatory, antibiotic, and/or antiseptic properties (Simchi, 2011).

More than One Coated Surface

Reference is now made to FIGS. 5A-5D which schematically illustrate perspective views in whole or sectionally, and/or in detail 610, 620, of exemplary coated bone plate 600 coated on at least one chamfer surface 640, 650 and/or rim surface 655, in accordance with some exemplary embodiments of the present invention.

In some exemplary embodiments of the invention, a bone plate implant 600 is coated by coating layer 630 over a surface 605 which may include details such as one or more chamfered surfaces 650, 640, and/or rim surfaces 655.

Coated surface 605 of bone plate 600, when implanted, may not be in contact with bone. However, other potential coating advantages discussed in relation to the coating of non-wearing surfaces FIGS. 4A-4D apply as well to the embodiments of FIGS. 5A-5D; for example, modification of surface properties. In another example, the shape-locking advantage described in connection with holes in FIGS. 2A-2D may also be provided.

Reference is now made to FIGS. 6A-6D which schematically illustrate perspective views in whole or sectionally, and/or in detail 710, 720, of exemplary coated bone plate 700 coated on at least two surfaces 705, 707, and having at least one region where coating layers 730, 735 overlap, in accordance with some exemplary embodiments of the present invention.

In some embodiments of the invention, a top-surface coating layer on a bone plate interacts with a bottom-surface (bone-facing) coating layer, for example by overlapping edges. This may provide the advantage of helping to restrain an overlapped layer against the body of a bone plate implant.

In some exemplary embodiments of the invention, a bone plate implant 700 is coated by at least two coating layers 730, 735 which cover at least portions of bone implant surfaces 705, 707, and furthermore overlap in at least one region covering a bone implant surface 740, 750.

In some embodiments, the wrap-around forms of coating layers 730, 735 may provide an independent shape-locking advantage, as previously discussed. Another potential advantage arises from the region of overlap, wherein an edge region of coating layer 735 is retained by overlapping coating layer 735. In some embodiments, one coating layer may extend around the implant to overlap itself in similar fashion.

According to the embodiment of the invention, the materials of bottom-surface coating layer 735 and top-surface coating layer 730 are the same, or different.

Optionally, in embodiments where materials are different, they are chosen such that the bottom-surface (bone-contacting) layer 735 material is optimized for a surface property, such as hardness. A potential advantage of using the geometry of the layers, (in particular regions of overlap) to mutually restrain one another is, for example, that the hard material may be chosen for use even having relatively poor properties of adherence to the underlying bone plate implant material (for example a titanium foil). Optionally, the materials are chosen to be galvanically inert with respect to each other.

Constraints affecting material choice may be different for top-surface layer 730 material. In some embodiments, top-surface layer 730 is chosen to have good adherence properties to the bone plate implant material, for example, PEEK. In restraining the edge regions of the lower-surface coating 735, the top-surface coating 730 potentially confers some of the advantage of its own adherence properties. In some embodiments, the top-surface coating is constructed to improve the stability of its restraining function; for example, it has a greater thickness, and/or is a material which assumes a relatively rigid form in the finished bone implant. Some of these embodiments are produced, for example, in one or in separate compression molding steps.

Pin Retaining Structures

Reference is now made to FIGS. 7A-7E which schematically illustrate perspective views in whole or sectionally, and/or in detail 810, 820, of exemplary coated bone plate 800 coated on at least one surface 805, 807, 850, 860 and having at least one region where a coating layer 830, 835 is held in place by a pin formation 825, 827, 828, 829, in accordance with some exemplary embodiments of the present invention. In some embodiments, pin formations are integral to the implant. In some embodiments, pins may be supplied as components which become attached to the body of the implant during manufacturing, for example, during pressure molding.

In some exemplary embodiments of the invention, a bone plate implant 800 is coated by at least one coating layer 830, 835 which covers at least portions of bone implant surfaces 805, 807. Coating layer 830, 835 has at least one aperture shaped and sized to accommodate a pin formation 825, 827, 828, 829 which acts as a retaining structure, tending to restrain the coating layer to the surface 805, 807, 850, 860 of the bone plate implant body. Pin formations 825, 827, 828, 829 are attached at a base end to the body of the bone plate implant. In some embodiments, they fill the aperture they occupy. In some embodiments, they act as a restraint without completely filling the aperture they occupy; for example, by having an annular cross-section. In some embodiments, they rise to a level which is about flush with the surrounding coating layer material. In some embodiments, pin formations 825, 827, 828, 829 comprise a shank that fits into the aperture, and a cap which interferes with the removal of a coating layer. In some embodiments, pin formations 825, 827, 828, 829 have a flange which covers an edge region of the surrounding coating layer. Optionally, a pin formation 825, 827, 828, 829 may protrude above or remain below or at the surface of the surrounding coating layer material.

According to the embodiment, the shank of a pin formation and/or the coating aperture it occupies may have a minimum cross-sectional dimension of, for example, 0.2 mm, 0.5 mm, 1 mm, 2 mm, 5 mm, or any dimension in between; or a larger or smaller dimension. A pin formation cross section may be circular, square, oblong, or another shape suitable for restraining the coating layer material; for example, a curved strip.

Some exemplary details of pin formation (retaining structure) form and manufacture are discussed in relation to FIGS. 9A-9C, 11A-11C, and 12A-12D.

In some embodiments of the invention, there are at least two coating layers 830, 835 which overlap and/or abut in at least one region covering a bone implant surface 850, 860; and both contain and/or together define at least one common aperture shaped and sized to accommodate a pin formation 825, 827, 829 which acts as a retaining structure on the coating layers it abuts and/or partially overlies. In some embodiments of the invention, a bone implant surface 860, which is coated by at least one coating layer 830, 835, may be constructed with a curvature shaped to help anchor the coating layer. Surface 860, for example, is illustrated with a concave curvature through the thickness of the bone implant, while having a convex curvature around its end. The degrees of freedom of the coating layer to move are restricted by this geometry, compared, for example, to a straight coating edge. A potential advantage of constructing a bone implant surface with different curvatures is to provide enhanced shape-locking.

Reference is now made to FIGS. 8A-8E which schematically illustrate perspective views in whole or sectionally, and/or in detail 910, 915, 920, of exemplary coated bone plate 900 coated on at least one surface 905, 907, 950, 960, 970 and having at least one region where a coating layer 930, 935 is held in place by an elongated pin formation 925, 927, 928, 929, in accordance with some exemplary embodiments of the present invention.

In some exemplary embodiments of the invention, a bone plate implant 900 is coated by at least one coating layer 930, 935 which covers at least portions of bone implant surfaces 905, 907, 950, 960, 970. Coating layer 930, 935 has at least one aperture shaped and sized to accommodate a pin formation 925, 927, 928, 929 which acts as a retaining structure, tending to restrain the coating layer to the surface 905, 907, 950, 960, 970 of the bone plate implant body. Optionally, two or more coating layers may share an aperture and pin. In contrast with the circular cross-section pin structures of FIGS. 7A-7E, FIGS. 8A-8E show elongated pin structures having various forms, including a straight bar 927, a convex bar 925, a concave bar 928, and a bar curved in the plane of the coating surface 929. In some embodiments, pin caps from two or more shanks merge, creating a "staple" geometry which restrains the coating layer. These examples may serve to illustrate some of the variety of retaining structures contemplated, and which may be produced by someone skilled in the art working according to descriptions herein.

Figure 9B:
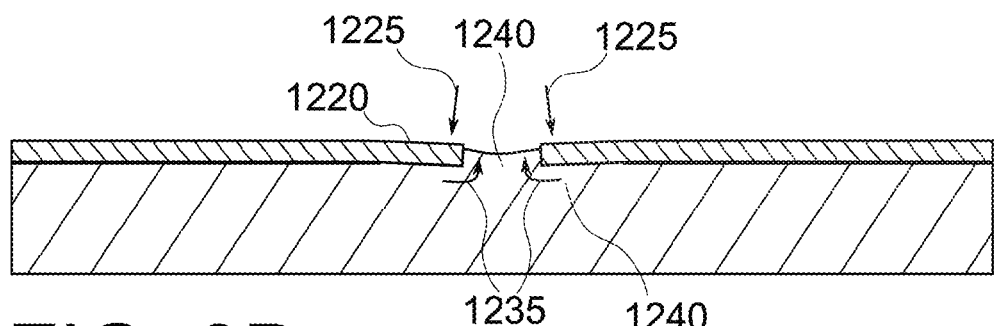
Figure 9C:
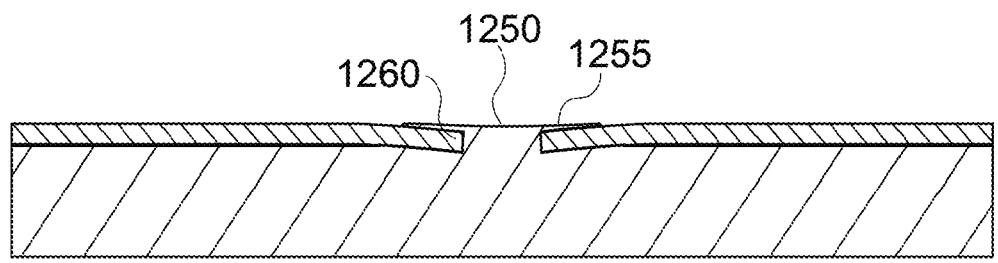

Reference is now made to FIGS. 9A-9C which schematically illustrate sectional views of phases in the extrusive formation of a retaining structure 1250 for restraining a coating layer 1200 to the body 1210 of a bone plate implant, in accordance with some exemplary embodiments of the present invention. These phases are illustrative, provided for the sake of assisting an understanding of aspects of some embodiments of the invention, and details may vary. Actual extrusion is accomplished by operations controlled through parameters determined at the macroscopic level.

FIG. 9A shows the material of a surface layer 1200 having an aperture 1205 overlying the body 1210 of a bone plate implant. In some embodiments of the invention, surface layer 1200 is a metal foil, for example of titanium or a titanium alloy.

FIG. 9B shows an intermediate stage in structure formation occurring under a sufficient inward pressure 1225 and/or temperature, as, for example, occurs during compression molding. Parameters of compression molding, including pressure and temperature, disclosed herein as being appropriate to inducing layer/matrix integration are also appropriate to extrusion formation. Pressure forces melted and/or plasticized bone plate material 1240 to fill the aperture 1205, according, for example, to lines of flow 1235.

As flow occurs, regions 1220 of surface layer 1200 which adjoin aperture 1205 may partially collapse. The degree of collapse may depend, for example, on the distances over which flow occurs, the stiffness of the foil, and the shape of the mold (which may have protrusions that submerge the foil while allowing matrix material to flow around them).

FIG. 9C shows a formed retaining structure, 1250, which in the embodiment shown includes flanges 1255 formed by backflow which serve to encase an edge region 1260. In some embodiments, formation of retaining structure 1250 during compression molding is encouraged by leaving spaces in the mold above a place where a retaining structure is desired. In some embodiments, formation of retaining structure 1250 during compression molding is encouraged by defining one or more apertures in the coating material before compression molding. In some embodiments, formation of retaining structure 1250 during compression molding is encouraged by adding material (for example an annulus) to the mold surface above a place where a retaining structure is desired, so that the coating layer is bent slightly inward under pressure.

Not all aspects of the above model of restraint of a coating layer to a bone plate implant body by an extrusion are required for an embodiment to function. Flanges are not to scale. They may, for example, be relatively larger or smaller; and/or thicker or thinner. A flange may extend, for example, for a length as long as the radius and/or width of the aperture, or 2 times the aperture size, 4 times the aperture size, 10 times the aperture size, or a longer or shorter distance or any distance in between. The depth of the material protruding above the coating layer may be, for example, 10% of the layer thickness, 20% of the layer thickness, 100% of layer thickness, 1000% of the layer thickness, a larger or shorter depth, or any depth in between. In some embodiments, they are absent. In some embodiments, restraint is accomplished, for example, by extrusion interactions with a thin end of the coating layer. In some embodiments, there is no collapsed region; as, for example, under conditions where substrate flow is sufficiently fluid. In some embodiments, flow-like plastic deformation of the coating material (not shown) occurs. Potentially, this also contributes to coating restraint.

Multi-layered Coatings

Reference is now made to FIGS. 10A-10D which schematically illustrate perspective views in whole or sectionally, and/or in detail 110, 120, of exemplary coated bone plate 100 coated on at least one surface 105 by at least two coating layers 125, 130, in accordance with some exemplary embodiments of the present invention.

In some exemplary embodiments of the invention, coated bone plate 100 is coated on at least one surface 105 by at least two coating layers 125, 130.

In some embodiments of the invention, innermost coating layer 130 is comprised of a different material than an overlying coating layer 125. In some embodiments, the material of an inner coating layer 130 comprises a bonding layer between an outer surface 140, 150 of the uncoated bone plate material, and an overlying coating layer 125. In some embodiments, an inner coating layer 130 is chosen that will flow under conditions of compression molding to produce retaining structures, such as are described, for example, in FIGS. 7A-7E and 8A-8E. In some embodiments, inner coating layer 130 comprises an elastic material, such as a silicon polymer. A potential advantage of an elastic inner coating is to distribute stresses at points of contact between bone and implant. In some embodiments, inner coating layer 130 comprises a one or more components of a self-healing system, for example, as described above.

Optionally, the outer surface 140, 150 material is PEEK. Optionally, the outer surface material 140, 150 comprises PEEK and carbon fiber. Optionally, the material of an inner coating layer 130 is PEEK. Optionally, the material of an outer coating layer 125 is a foil of metal, for example titanium or a titanium alloy.

In some embodiments of the invention, materials of different layers within the volume of a composite implant are chosen to adjust another property of the implant. For example, the material may be chosen for its thermal characteristics, electrical properties such as conductivity and capacitance, for its relative permeability and/or imperviousness to one or more wavelengths of electromagnetic radiation, or another material property. High thermal conductivity, for example, may provide an advantage for reducing potentially damaging heat buildup at drilling sites. A relatively high thermal coefficient of expansion may be taken advantage of in some embodiments to allow, for example, shrink fitting a layer heated during manufacture over an inner core to achieve a firmer attachment upon cooling. In some embodiments, conductivity and/or capacitance are used in connection, for example, with sensing and/or telemetry (sensing and telemetry are also related to hereinbelow). Potential advantages for a predetermined electromagnetic opacity are described, for example, in relation to FIGS. 16A-16B, hereinbelow.

Figure 11A:
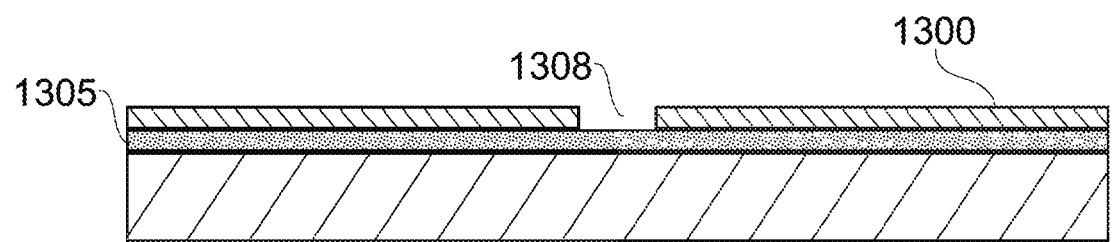
FIGS. 11A-11C schematically illustrate sectional views of phases in the extrusive formation of a retaining structure for restraining a coating layer to the body of a bone plate implant, in accordance with some exemplary embodiments of the present invention.
Figure 11B:
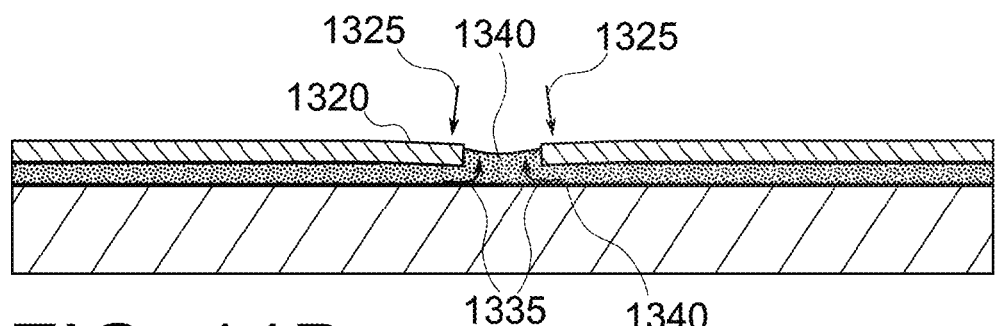
Figure 11C:
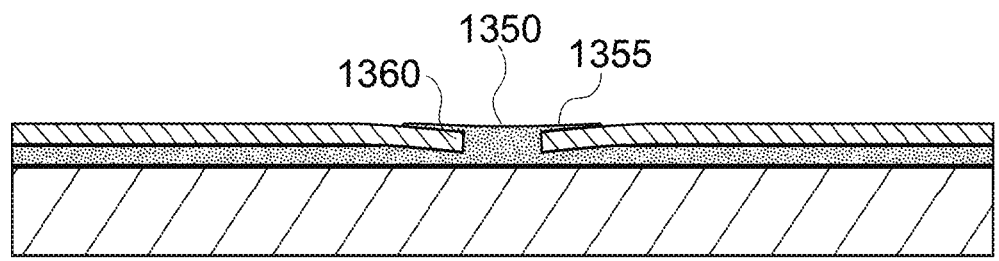
Figure 12A:
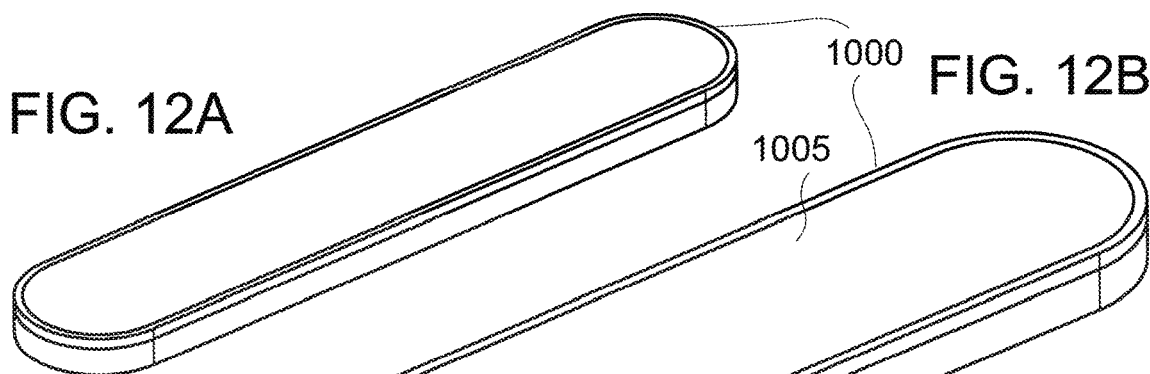
FIG. 12A schematically illustrates a perspective view of an exemplary coated bone plate coated on at least one surface and having at least one region where a coating layer is held in place by a retaining structure, in accordance with some exemplary embodiments of the present invention.
Figure 12B:
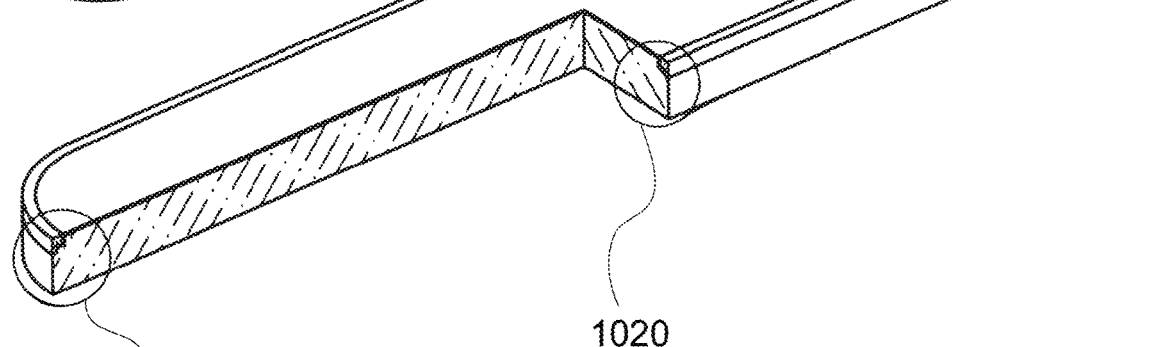
FIGS. 12B-12D schematically illustrate perspective, sectional views of the bone plate of FIG. 12A in overview and/or in detail, in accordance with some exemplary embodiments of the present invention.
Figure 12C:
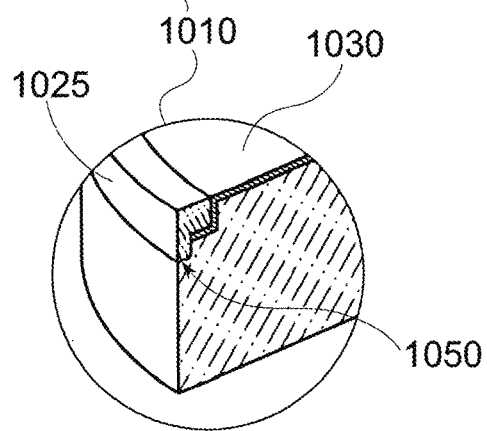
Figure 12D:
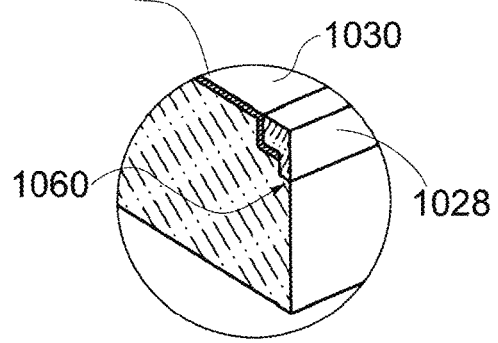

Reference is now made to FIGS. 11A-11C which schematically illustrate sectional views of phases in the extrusive formation of a retaining structure 1350 for restraining a surfacing layer 1300 in the presence of an underlying layer 1305, in accordance with some exemplary embodiments of the present invention.

The phases of FIGS. 11A-11C are congruent with the phases of FIGS. 9A-9C. These phases are illustrative, provided for the sake of assisting an understanding of aspects of some embodiments of the invention, and details vary according to the embodiment.

FIG. 11A adds to the surface layer 1300, aperture 1308 and bone plate implant body 1300 an underlying layer 1305 which is provided with material properties appropriate to serve as the source of extrusion material.

FIG. 11B shows an intermediate stage in structure formation occurring under a sufficient inward pressure 1325 and/or temperature, as, for example, occurs during compression molding. Parameters of compression molding, including pressure and temperature, disclosed herein as being appropriate to inducing layer/matrix integration are also appropriate to extrusion formation. Pressure forces melted and/or plasticized bone plate material 1340 to fill the aperture 1305, according, for example, to lines of flow 1335.

As flow occurs, regions 1320 of surface layer 1300 which adjoin aperture 1308 may partially collapse. The degree of collapse may depend, for example, on the distances over which flow occurs.

FIG. 11C shows a formed retaining structure 1350, which in the embodiment shown includes flanges 1355 formed by backflow which serve to encase an edge region 1360. In some embodiments, formation of retaining structure 1350 during compression molding is encouraged by leaving spaces in the mold above a place where a retaining structure is desired.

A potential advantage of using underlying layer 1305 as a source of fill material is the ability to select filling characteristics different than those of the bulk material of the bone plate implant. Optionally, the material of underlying layer 1305 provides an extruded appearance which masks the color of the bone implant body.

Optionally, the material of underlying layer 1305 is selected so that it flows at a higher or lower temperature than the bulk material of the bone plate implant. This may provide an advantage, for example, if a heat-sensitive agent, such as a healing agent, is to be provided as part of the bone plate implant construction.

Not all aspects of the above model of restraint of a coating layer to a bone plate implant body by an extrusion are required in an embodiment for function. Exceptions and alternatives are discussed herein in relation to FIGS. 9A-9C.

Retaining Strip

Reference is now made to FIGS. 12A-12D which schematically illustrate perspective views in whole or sectionally, and/or in detail 1010, 1020, of exemplary coated bone plate 1000 coated on at least one surface 1005, and having at least one region where a coating layer 1030 is held in place by a retaining strip 1025, 1028, in accordance with some exemplary embodiments of the present invention.

In some embodiments of the invention, one or more lengths of retaining strip 1025, 1028 are provided. Optionally, retaining strip 1025, 1028 is made, for example, from PEEK, PEKK, or another suitable material. Optionally, retaining strip lengths 1025, 1028 are portions of a single strip length. Optionally, retaining strip lengths 1025, 1028 form a contiguous circumference. In some embodiments, retaining strip 1025, 1028 is formed, for example, with a stepped structure, such that it fits into a complementary recess in the body of exemplary bone plate 1000.

In some embodiments, material for forming coating layer 1030 is cut so that it may protrude into the recessed region of bone plate 1000 when it is placed over bone plate surface 1005. While it is so placed, retaining strip 1025, 1028 inserts into the recess, such that one or more edge regions of coating layer 1030 are trapped between the strip, 1025, 1028, and the body of bone implant 1000.

In some embodiments, retaining strip 1025, 1028 is bonded to the underlying bone implant material, for example along surfaces 1050, 1060. Optionally, the bonding occurs under compression molding conditions.

In some embodiments of the invention, an inserted retaining strip is located within a circumferentially enclosed aperture of a coating layer. Optionally, it is reduced to the size and shape of a plug. Optionally, such a plug-like insert may not have a complementary recess in the body of a bone plate, and be bonded instead to the flat surface of the body. In some embodiments, this is an alternative to the extrusion steps described in FIGS. 9A-9C for producing, for example, restraining pins 828, 825, 827, 829, 929, 925, 927, 930 such as are described in connection to FIGS. 7A-7E, and/or FIGS. 8A-8E.

The use of inserted material for retaining a coating layer provides a potential advantage by allowing pin, plug, and/or strip material to be chosen which has different properties than the underlying bone plate implant material. For example, it may be of different appearance, or have different melting or pressure deformation characteristics than the material of the underlying implant. Potentially, this allows the conditions of pressure molding to be different, optionally less stringent (lower pressure or temperature) than otherwise required. Potentially, this allows the appearance of the underlying bone plate implant body to be entirely masked by either the coating material or the insert material. In some embodiments, the insert material may itself be structured, for example, to contain radio-opaque marker material as part of the retaining pin, plug, or strip.

Combinations of Restraint Types

Figure 13A:
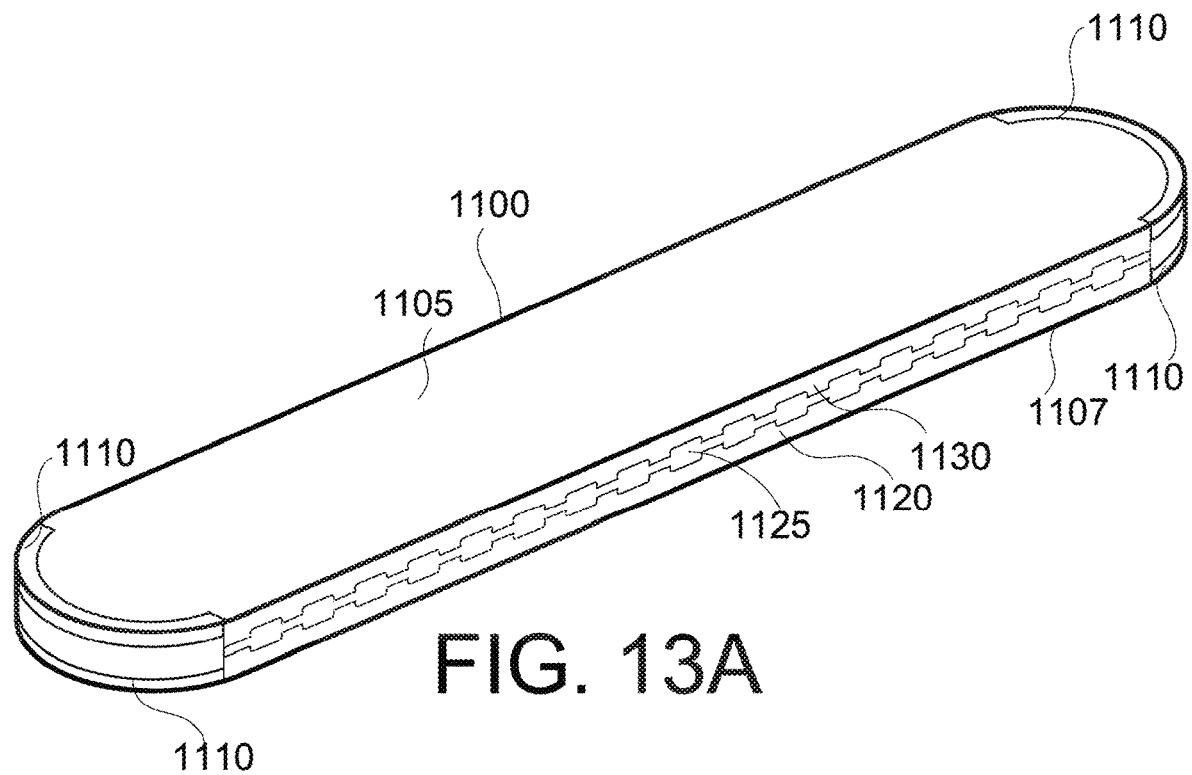
FIG. 13A schematically illustrates a perspective view of an exemplary coated bone plate coated on at least one surface and having regions where a coating layer is held in place by one or more retaining structures, in accordance with some exemplary embodiments of the present invention.

Reference is now made to FIG. 13A which schematically illustrates a perspective view of exemplary coated bone plate 1100 having coating layer regions held in place by one or more retaining structures 1110, 1125, in accordance with some exemplary embodiments of the present invention. This drawing illustrates some of the variety of retaining structure contemplated in the current invention.

In some embodiments of the invention, retaining strips 1110 (lengths of strip like restraining strip 1025), are non-continuous around the edges of one or more layers 1130, 1120, restraining these layers to corresponding bone plate implant surfaces 1105, 1107 only in predetermined places; for example, on the ends of the bone plate.

In some embodiments of the invention, elongated retaining structure 1125 is a protrusion restraining one or more layers 1130, 1120 to corresponding bone place surfaces 1105, 1107 by one or more of the mechanisms described in connection with elongated restraining pin 925. In some embodiments, elongated retaining structure 1125 is not circumferentially surrounded by the material of any single layer. In some embodiments, the upper and/or lower contours of elongated retaining pin 1125 are non-straight, as shown. This provides the potential advantage of improved retaining by gripping retained edges over a longer interfacing extent, and/or from multiple directions. Optionally, the contours of elongated structure 1125 are straight.

In some embodiments of the invention, retaining structure 1125 is produced by compression molding. The material of one or more coating layers 1130, 1120 is pre-cut with an edge conforming to the intended outline of elongated retaining structure 1125 at the place where they will contact. Under compression molding, bone plate material undergoes plastic and/or fluid flow. Constrained by edges including the pre-cut edges of coating layers 1130, 1120 some of this material comes to comprise retaining structure 1125.

Optionally, bone plate 1100 is coated only on one side. Optionally, retaining structure 1125 has a retaining edge only on one side, for example, on an upper or a lower side. In some embodiments, the other edge is unformed, as occurs under compression molding when only one coating layer is provided.

It should be appreciated by someone skilled in the art that the retaining structures herein described are susceptible to combination on a single embodiment of the invention. Exemplary bone plate 1100, for example, combines a partially circumferential retaining strip 1110 with an elongated retaining structure 1125.

According to the embodiment of the invention, any suitable number, density, and/or relative arrangement of restraining structures is used. For example, restraining structures may occur with a spacing of 1 mm, 2 mm, 5 mm, 10 mm, 20 mm, or 50 mm. or any distance in between, or distances larger or smaller. In some embodiments, restraining structures may occur with a spacing defined relative to the overall length or width of the implant, over part or all of one or more implant surfaces; for example every 1% of the implant length or width, every 2%, every 5%, every 10%, or any distance in between, or distances larger or smaller. Restraining structures are spaced regularly or irregularly. Optionally, restraining structures are concentrated in one or more regions. Optionally, restraining structures are spread across a whole surface.

Figure 13B:
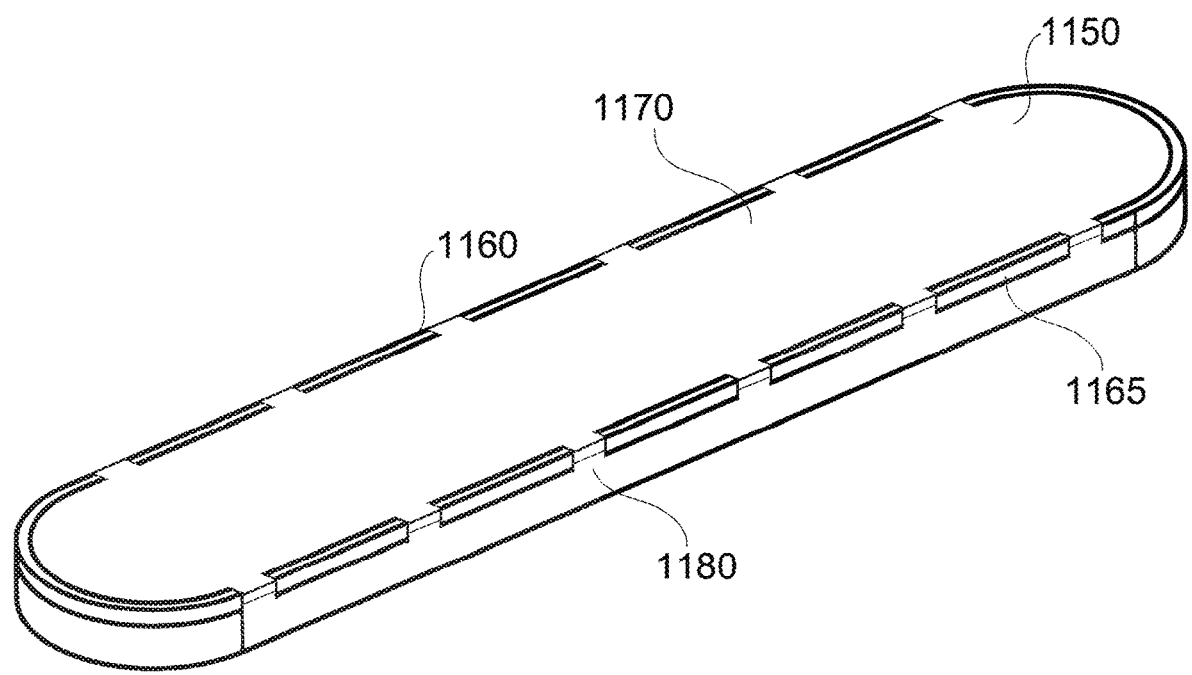
FIG. 13B schematically illustrates a perspective view of an exemplary coated bone plate coated on at least one surface and having regions where a coating layer is held in place by one or more retaining structures, in accordance with some exemplary embodiments of the present invention.

Reference is now made to FIG. 13B which schematically illustrates a perspective view of exemplary coated bone plate 1150 having coating layer regions held in place by one or more retaining structures 1160, 1165, in accordance with some exemplary embodiments of the present invention. This drawing illustrates some of the variety of retaining structure contemplated in the current invention.

In some embodiments of the invention, retaining strips 1160, 1165, are non-continuous around the edges of one or more layers 1170, 1180, restraining them to underlying bone plate implant surfaces only in predetermined places. In some embodiments, restrained layers come together at an angle, and the orientations of the surfaces of attachment for retaining strips 1160, 1165 are different from one another. For example, retaining strip 1160 may attach to a horizontal (top-or bottom-surface) plane, as shown for retaining strip 1025, while retaining strip 1165 attaches to a vertical (side surface) plane, in order to secure the edge of vertically approaching layer 1180. In some embodiments of the invention, portions of a partially coated surface are left uncoated. This may provide an advantage, for example, in order to be drilled into without disturbing the coating fixation at other points. In some embodiments, regions left uncoated have different material properties than coated regions; for example, material in a region intended for potential drilling is selected for fracture toughness in preference to providing stress strength.

In some embodiments of the invention, regions of attachment between retaining strips and the underlying material of the bone plate are determined in part by the shape and extent of retained layer edges. For example, edges of layers 1170, 1180 are cut to be non-straight. In some embodiments, cuts and protrusions of the trapped edges of layers 1170, 1180 are interdigitated. This allows one retaining strip 1160 to be exposed to both vertically and horizontally-oriented bone plate surfaces underneath. In some embodiments, regions of exposure convert under pressure molding conditions into regions of attachment, securing more than one approaching edge under one retaining strip.

Apertured layers

Reference is now made to FIGS. 14A-14D which schematically illustrate perspective views in whole or sectionally, and/or in detail 1410, 1420, of exemplary coated bone plate 1400 having an aperture-patterned layer 1430 on at least one surface 1407, in accordance with some exemplary embodiments of the present invention. In some embodiments, aperture-patterned layer 1430 is made of metal, for example titanium. In some embodiments, aperture-patterned layer 1430 is made of a material which is radio-opaque relative, for example, to the bulk material of the bone plate implant body.

A potential advantage of a coating which comprises a radio-opaque grid, mesh, screen, grating and/or other apertured structure 1460 is to outline and/or locate all or part of the bone implant in radiographic images. Outlining and/or position indication in a radiographic image is provided by the portions of the apertured structure 1460 which are radio-opaque. Another potential advantage of an apertured structure is partial radiographic transparency due to the incomplete coverage of the bone implant. This potentially permits radiographic visualization of bone and/or other structures behind the outlined and/or position indicated bone implant which might otherwise be obscured.

A potential advantage of an apertured coating is to provide additional flexibility to the coating. In some embodiments, apertures are provided to the coating layer according to the position of screw holes. This may provide an advantage for manufacturing; for example, by allowing the coating to conform to irregular features of the bone implant without tearing and/or bunching. According to the embodiment, apertures, slits, and other adjustments to the pattern of the coating layer are created before attachment to the bone implant body. A mesh of apertures may be prepared from an extended-surface material substrate; for example by stamping, perforating, slitting, cross-overlaying two or more sub-layers, or by another method known in the art. A mesh of apertures may be prepared from strip or wire material; for example by weaving, knitting, winding at crossed angles or by another method known in the art.

In some embodiments, the prepared layer is matched to the bone implant body during attachment steps so that features such as apertures align with appropriate underlying structures.

In some exemplary embodiments of the invention, a bone plate implant 1400 is coated by apertured layer 1430, which at least partially covers surfaces of the bone implant; for example surface 1440 and/or surface 1450.

Reference is now made to FIGS. 15A-15D which schematically illustrate surface views of exemplary aperture patterns usable in some embodiments to comprise apertured layer 1430, in accordance with some exemplary embodiments of the present invention.

Figure 15A:
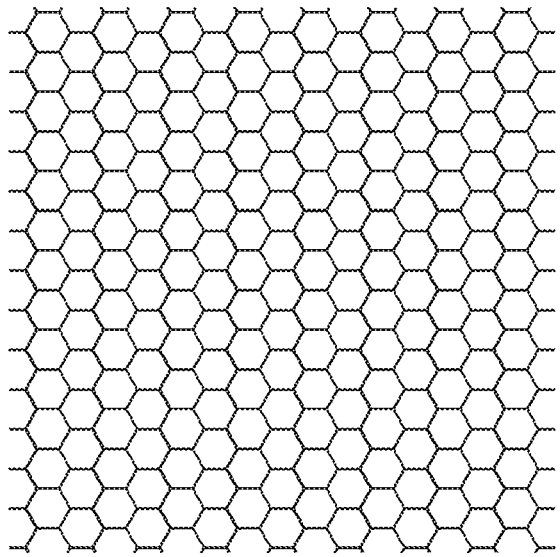
FIGS. 15A-15D schematically illustrate surface views of exemplary aperture patterns used in some exemplary embodiments to comprise a mesh (apertured) layer, in accordance with some exemplary embodiments of the present invention.
Figure 15B:
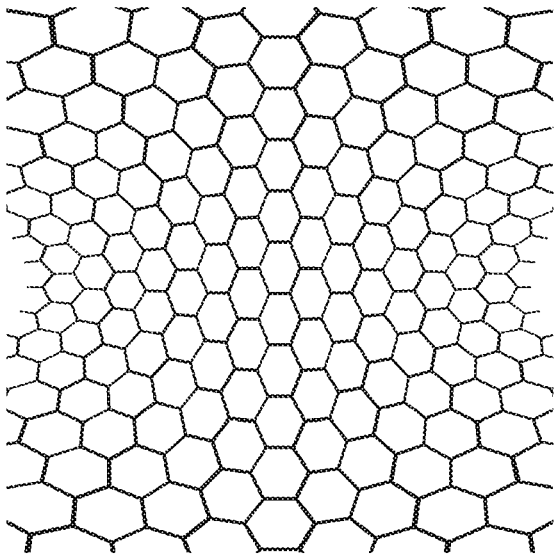
Figure 15C:
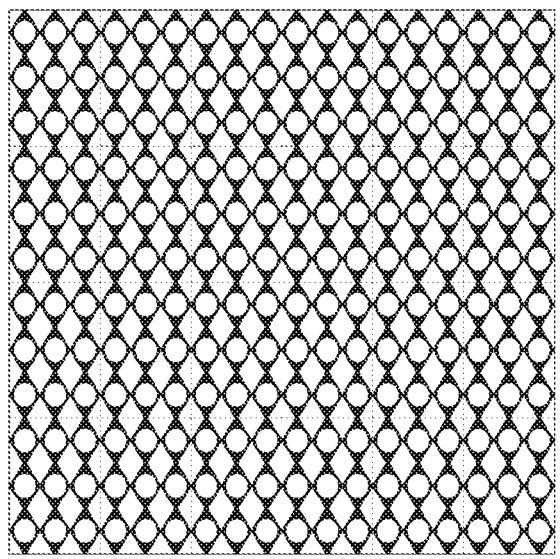
Figure 15D:
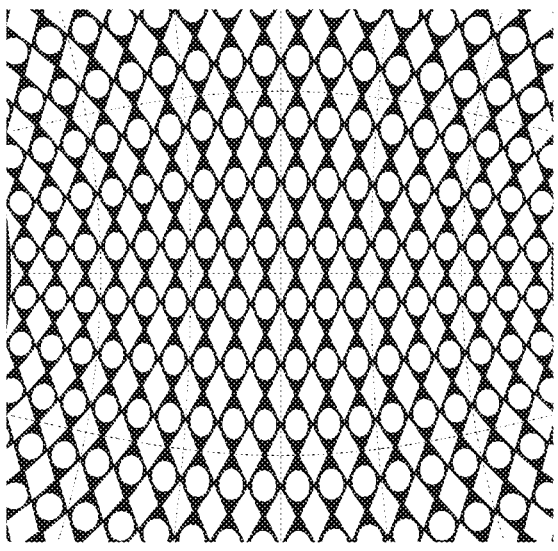

In some embodiments, the apertures of layer 1430 comprise, for example, 10% of its area extent, 20% of its area, 50% of its area, 90% of its area, or another greater or smaller percentage of its area. In some embodiments, apertures are uniform. For example, FIG. 15A shows a pattern of uniform hexagonal apertures. In some embodiments, the shape of the apertures of layer 1430 is, for example, triangular, circular, square, rectangular, or another shape. In some embodiments, more than one aperture shape is used. For example, FIG. 15C shows a pattern of apertures laid out on a rhombus grid, with aperture shapes alternating between circular and rhombus. In some embodiments, apertures are non-uniform in size and/or shape over the coated surface. For example, FIG. 15D shows a pattern like that of FIG. 15C, with the shapes distorted. According to the embodiment, distortion occurs during manufacturing, for example, to follow a curve of the bone implant device. In another example, FIG. 15B shows an irregular hexagonal pattern which is optionally formed as an initial pattern of apertures in layer 1430. A potential advantage of an irregular pattern is to allow tuning of the relative radio-opacity of different regions of the bone implant. Another potential advantage of an irregular pattern is to mitigate the formation of resonances due to a repeating structure which may produce imaging artifacts. Another potential advantage of an irregular pattern is to allow introducing differential susceptibility to distortion; for example, by using larger and/or more frequent holes in regions where the coating layer must bend through sharper angles to conform to the underlying surface. In some embodiments, the relative spacing of the apertures of layer 1430 is, for example, 0.1 mm, 0.5 mm, 1 mm, 5 mm, 10 mm, or another greater or smaller spacing. Optionally, the spacing of the apertures is uniform.

Alternatively, the spacing of the apertures is non-uniform over the coated surface.

According to the embodiment, the thickness of the apertured mesh structure (coating or embedded in the implant body) ranges, for example: between 100 nanometers and 1 micron, between 1 micron and 10 microns, between 10 microns and 100 microns, between 100 microns and 1 mm, and between 1 mm and 2 mm. In some embodiments, a different thickness is used at different regions of the implant.

According to the embodiment, layer 1430 is constructed, for example: of a perforated foil; of woven, knotted or braided wires; of overlaid wires or foil strips; of wound wire or foil stripping, or by another construction suitable for forming a structure of alternating apertures and radio-opaque material. In some embodiments, layer 1430 is comprised of a potentially unperforated polymer sheet to which an apertured pattern of a radio-opaque material has been attached, for example by spraying, painting, and/or dipping. In some embodiments, layer 1430 is applied together with one or more other layers. The pattern of apertures (or gaps) and aperture- or gap-defining material formed by layer 1430 may be striped; for example, as could be constructed by spirally winding one or more wires or foil strips, optionally of radio-opaque material, around a bone implant. According to the embodiment, the orientation of the pattern of apertures may be in any direction.

Figure 16A:
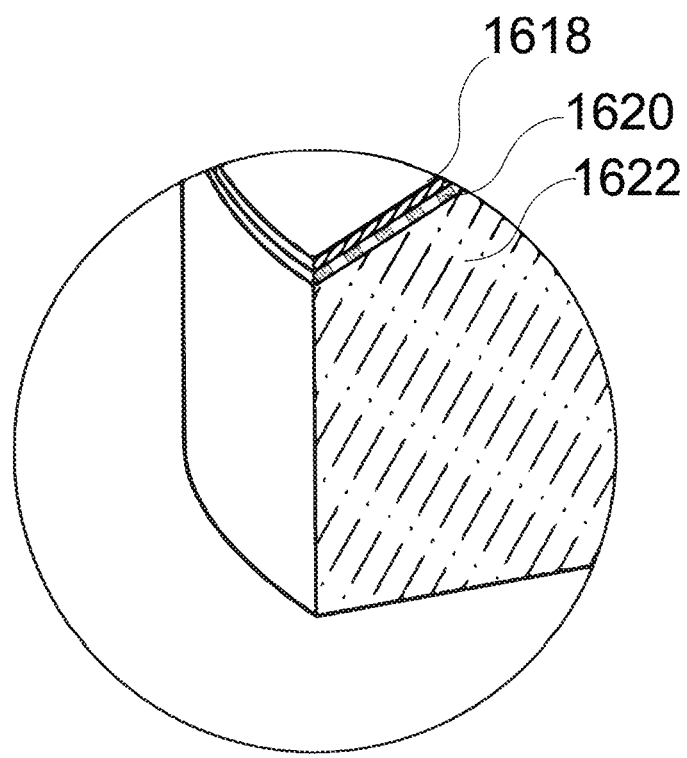
FIGS. 16A-16B schematically illustrate in perspective sectional view regions of exemplary bone having a mesh (apertured) structure embedded within the implant body, and/or underneath a coating layer, in accordance with some exemplary embodiments of the present invention.
Figure 16B:
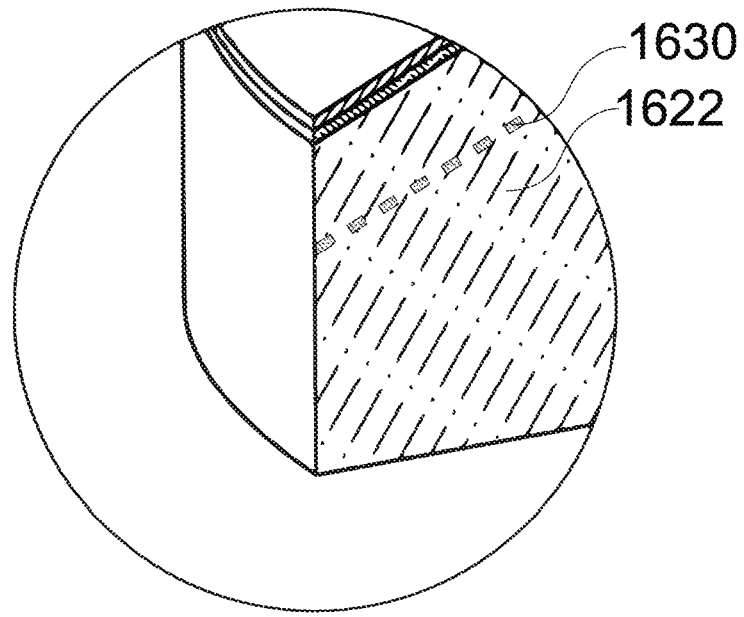

Reference is now made to FIGS. 16A-16B which schematically illustrate in perspective sectional view regions of exemplary bone implants (which are, for example, sized and shaped overall like exemplary coated bone plate 1400; or, alternatively, have the shape of another bone implant herein described, or of another bone implant shape known in the art) having an apertured layer 1620, 1630 embedded within the implant structure, in accordance with some exemplary embodiments of the present invention. In some embodiments, layer 1620 is overlaid on the body 1622 of a bone implant, and itself overlaid by an additional coating layer 1618. In some embodiments, layer 1630 is embedded within the material of the body 1622 of a bone implant; for example, during a stage of manufacturing in which the body is being originally formed. In some embodiments, an apertured layer 1620, 1630 is radio-opaque.

In some embodiments, the pattern of radio-opaque material formed by layer 1430 is chosen to minimize artifacts in magnetic resonance imaging (MRI) images. For example, the aperture size and/or spacing is chosen to reduce an amount of metal present in layer 1430. Optionally, the aperture size and/or spacing are adjusted to change the placement of material formed by layer 1430 so that artifacts affecting tissue visualization in MRI images are reduced. In some embodiments, the formation of eddy currents affecting MRI images is reduced by the apertures which break and thereby shorten the available pathways for current circulation.

In some embodiments, radio-opaque elements are provided as separate elements. Elements may be arranged in an encoding pattern for identification, and/or arranged to delineate the position of one or more features of the bone implant.

Encoding may be, for example, by providing a specific pattern of grouped elements, a specific number of grouped elements, and/or providing grouped elements with different relative transparencies. In some embodiments of the invention, radio-opaque elements are positioned on a coating layer before attachment of the coating with a predetermined location and/or orientation.

Materials which may be used in a radio-opaque marker include, for example, titanium, tungsten, barium sulfate, and zirconium oxide.

Identification and/or Telemetry

In some embodiments of the invention, one or more coating layers are provided with electronic circuitry. In some embodiments, the circuitry includes one or more radio frequency identification (RFID) tags which are interrogated to report an identifying code or other information. In some embodiments, patterning of the coating layer itself comprises a portion of the electronic circuitry, for example, an antenna for an RFID device. In some embodiments, an RFID device is embedded in the body of the bone implant. In some embodiments, the circuit provides biotelemetry through implementing a wireless identification and sensing platform (WISP) or other telemetry platform. In some embodiments, one or more biotelemetry circuits are provided with a sensor; for example, with a strain sensor. Optionally, the strain sensor senses multiple strain values through a range. Optionally, the strain sensor is a fuse-type sensor, which detects, for example by breaking, whether a preset strain level has been exceeded during the lifetime of the device. A potential advantage of strain sensing is to alert to the possibility of damage leading to device failure in a bone implant device.

Detail Coating

Figure 17A:
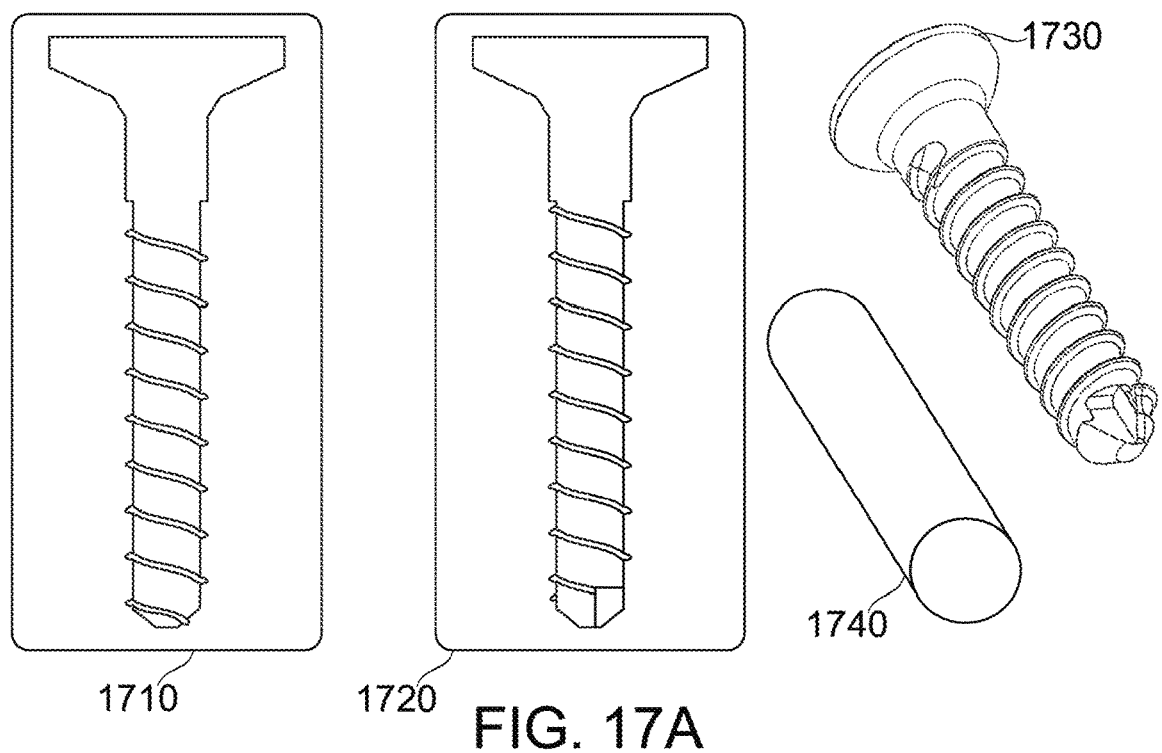
FIGS. 17A-17B schematically illustrate mold and part components for coating of a bone screw by compression molding, in accordance with some exemplary embodiments of the present invention.
Figure 17B:
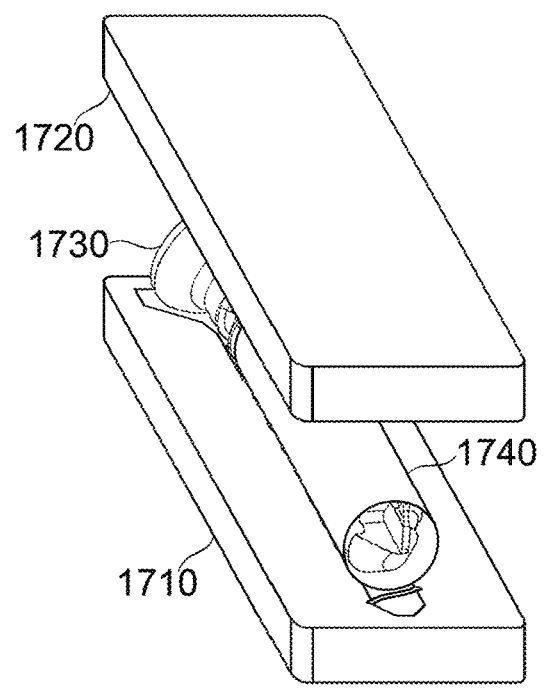

Reference is now made to FIGS. 17A-17B, which schematically illustrate mold and part components for coating of a bone screw by compression molding, in accordance with some exemplary embodiments of the present invention.

In some embodiments of the invention, manufacturing of a composite material implant comprises attachment by compression molding of a thin metal film to an implant surface comprising fine details. In some embodiments, the surface details to be coated comprise a screw thread, for example, the thread of a bone screw. In some embodiments, the coated surface details comprise another surface feature, such as identifying marks, raised or indented texturing, and/or fine cut-outs or protrusions.

In some embodiments, mold components 1710, 1720 comprise reverse-relief impressions accommodating the contours of the component 1730 to be coated.

Optionally, the impressions accommodate the contours with a gap sufficient for accommodating the coating layer as well, and/or the gap is optionally larger than needed for accommodating the coating layer. In some embodiments, component 1730 comprises a composite construction, such as carbon fiber-PEEK, or another composite construction, for example as described hereinabove.

In some embodiments, details of component 1730 to be coated comprise structures having a smallest dimension of, for example, 100-250 μm 200-500 μm, 400-800 μm, 500-1000 μm, or another larger or smaller range of smallest dimensions. A smallest dimension may be, for example, the distance across a thread protrusion, thread incision, and/or the thickness of a line in an embossed character. In some embodiments, a sharp radius of curvature is accommodated, for example, a radius down to a size of 50-100 µm, 75-150 µm, 100-250 µm, 200-500 µm, 400-800 µm, 500-1000 µm, or another larger or smaller curvature radius.

In some embodiments of the invention, the mold tolerances are predetermined so that the mold itself directly presses the coating layer to the part to be coated. In some embodiments, the mold tolerance is larger. Optionally, a pressing fit is obtained, for example, by use of an outer material for filling gaps in the mold. The filler material is, for example, PEEK, or another plastic resin suitable for compression molding together with the component, for example as described in connection with compression molding hereinabove. Optionally, the outer filler material is removed after compression molding, leaving behind the coated component 1730.

In some embodiments, the coating material is a thin metal foil 1740, comprising, for example, titanium, titanium alloy and/or stainless steel. In some embodiments, the coating material is a polymer 1740, comprising, for example, PEEK and/or PEKK.

The thickness of the metal film is, for example, 2-20 µm 10-40 µm, 25-50 µm, 40-80 µm, 50-100 µm, 75-150 µm, 140-200 µm, a wider or narrower range of thicknesses, or range comprising thicker or thinner film thicknesses.

In some embodiments, another coating material is used, for example a tape or other coating material as described in connection with other coated embodiments hereinabove. In some embodiments, the coating material is placed within the mold 1710, 1720 between the mold surface and the material of the component to be coated.

In some embodiments, the coating material is placed as a winding, a sheet, a tube, or in another for suitable for bringing the coating material into close association with the component to be coated. In some embodiments, the coating material is previously shaped with a screw thread or other shape, for example to accommodate the thread of a bone screw. Optionally, another preparation of the coating material forms it into a shell for fitting more closely to the component to be coated before a compression molding process.

In some embodiments, the coating material undergoes a compression molding process together with the coated component.

In some exemplary embodiments of the invention, the molding process results in the adhesion of a metal foil to the material of the coated component. Potentially, this confers an increase resistance to shear forces (forces parallel to the metal film). In some embodiments, the advantage conferred is another of the advantages described in connection with different coatings described hereinabove.

In some embodiments, adhesion is less resistant to forces perpendicular to the metal foil or other coating material. Optionally, the metal shell is peelable from the component after removal from the mold. A potential advantage for a peelable shell is to reduce adherence of a composite material to the mold as a result of compression molding. Another potential use of a peelable shell is to use the preformed shell shape to impress onto the component shapes (for example, an inner thread for a hole) which are difficult to non-destructively release from a mold block.

Bone Nail Coating

Figure 18:
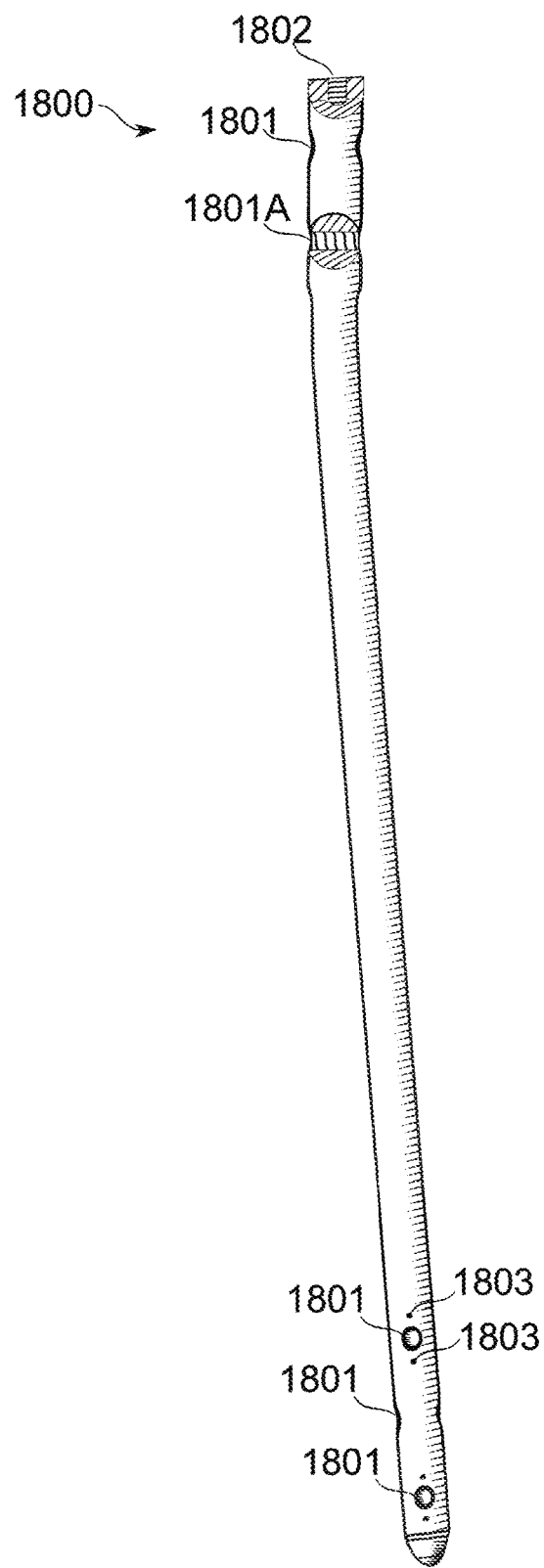
FIG. 18 schematically illustrates a bone nail coated with PEEK by compression molding, in accordance with some exemplary embodiments of the present invention.

FIG. 18 schematically illustrates a bone nail coated with PEEK by compression molding, in accordance with some exemplary embodiments of the present invention.

In some embodiments, a coated bone implant comprises a composite-construction bone nail (intramedullary nail) 1800. In some embodiments, the body of the composite-construction bone nail is comprised of carbon fiber-PEEK composite.

In some embodiments, a composite-construction bone nail is coated with PEEK using compression molding, for example as described hereinabove for bone implants of other shapes and/or types. In some embodiments, a bone nail 1800 is wrapped in a PEEK tape, and undergoes a compression molding step. In some embodiments, an added layer of PEEK does not comprise carbon fibers and/or another fiber reinforcement material present in the underlying composite construction.

Potential advantages of this include modification of a surface appearance, modification of the amount and/or appearance of particle shedding, and/or other potential advantages as described hereinabove in relation to bone implant coatings for bone implants such as bone plates and bone screws. In some embodiments of the invention, another composite-construction bone implant component is coated with a superficial layer of PEEK, for example, a bone plate and/or a bone screw.

In some embodiments, bone nail 1800 comprises radiopaque markers 1803. In some embodiments, radiopaque markers 1803 are added to bone nail 1800 during the compression molding operation, for example by adding the markers underneath a wrapping PEEK tape or by otherwise incorporating them along with the wrapping material.

In some embodiments of the invention, bone nail 1800 comprises holes 1801, 1801A, 1802. In some embodiments, holes are threaded (seen in cross-section at holes 1801A, 1802). Holes 1801, 1801A, in some embodiments, comprise holes for receiving bone screws. Optionally, radiopaque markers 1803 are located near holes 1801, 1801A to assist in hole localization during implantation. In some embodiments of the invention, hole 1802 comprises a receiving hole for an implantation handle, which is optionally attached during implantation to assist in the implantation procedure. In some embodiments, one or more of holes 1801, 1801A, 1802 are coated and/or lined in a compression molding process, for example as described for bone plate holes hereinabove.

As used herein the term "about" refers to 10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

REFERENCES

S Beauvais, O Decaux; Plasma Sprayed Biocompatible Coatings on PEEK Implants.

S W Ha et al.; Topographical characterization and microstructural interface analysis of vacuum-plasma-sprayed titanium and hydroxyapatite coatings on carbon fibre-reinforced poly(etheretherketone), *Journal of Materials Science: Materials In Medicine* (1997) 8:891-896.

M A Rahamathunnisa et al.; Coatings on Composites, Lappeenranta University of Technology, Faculty of Technology, Department of Mechanical Engineering, Research Report No. 74, ISBN 978-952-214-504-8, ISSN 1459-2932, Mikkeli (2007).

E Lugscheider et al.; Magnetron sputtered titanium nitride thin films on thermoplastic polymers, *Surface and Coatings Technology* (1999) 116-119.

H S Kim, H J Jung Kim; Detorque force of TiN-coated abutment screw with various coating thickness after repeated closing and opening, *J Korean Acad Prosthodont* (2007) 45:1172-1178.

G Williams et al.; A self-healing carbon fiber reinforced polymer for aerospace applications, *Composites:* Part A (2007) 38: 1525-1532.

E T J Rochford et al.; In vitro investigation into bacterial adhesion to medical grade PEEK surfaces, 56th Annual Meeting of the Orthopedic Research Society (2010) Poster 666.

A Simchi et al.; recent progress in inorganic and composite coatings with bacterial capability for orthopedic applications, Nanomedicine: nanotechnology, biology and medicine (2011) 7:22-39

Xing Zheng et al.; lubrication of polyether ether ketone (PEEK) surface by liquid ultrathin films for high wear durability, *Wear* (2012) 296:681-692.

K Hargou et al.; Ultrasonic activation of mendable polymer for self-healing carbon-epoxy laminates, *Composite, Part B*, in press (2012).

E L Steinberg et al.; Carbon fiber reinforced PEEK Optima-A composite material biomechanical properties and wear/debris characteristics of CF-PEEK composites for orthopedic trauma implants, *J Mech Behav Biomed Mater*, (2013) 17:221-8.

ATI Ti-6A1-4V, Grade 5 technical data sheet VERSION 1 (Jan. 31, 2012).

What is claimed is:

1. A bone implant comprising:
   a body of fiber-reinforced polymer composite material; and
   at least one porous coating layer configured to contact bone when implanted, wherein said at least one porous coating layer includes apertures, wherein at least one exterior facing surface region of said body interacts with said apertures;
   wherein said at least one porous coating layer is made at least partly of a material such that the body is shielded from wearing contacts with bone when implanted; and
   wherein said at least one porous coating layer covers a portion of said body to provide partial radiographic transparency to said body.

2. The bone implant of claim 1, wherein said at least one porous coating layer includes at least one of titanium (Ti), titanium nitride (TiN), titanium aluminum nitride Ti—Al—N), a titanium ceramic, a titanium alloy, and titanium oxide.

3. The bone implant according to claim 1, wherein said at least one porous coating layer is formed by 3D printing.

4. The bone implant according to claim 1, wherein said body and said at least one porous coating layer are attached by compression molding.

5. The bone implant according to claim 1, wherein said fiber-reinforced composite material is at least partly integrated with said apertures.

6. The bone implant according to claim 1, wherein said at least one porous coating layer is at least partly embedded in said fiber-reinforced composite material.

7. The bone implant of claim 1, further including at least one radio-opaque element at least one of embedded in, overlying, and underlying at least one of said at least one coating layer.

8. The bone implant of claim 1, wherein at least one of said at least one coating layer is configured to provide high surface hardness to said implant.

9. The bone implant of claim 1, wherein said at least one coating layer is configured to promote osteo-integration of said implant.

10. The bone implant of claim 1, wherein a thickness of said at least one coating layer is in a range of one of: between 100 nanometers and 1 micron, between 1 micron and 10 microns, between 10 microns and 100 microns, between 100 microns and 1 mm, and between 1 mm and 2 mm.

11. The bone implant of claim 1, wherein said at least one coating layer is configured to at least one of present and release at least one pharmaceutically active material, after implantation.

12. The bone implant of claim 1, wherein said body is formed of PEEK and carbon fiber.

13. The bone implant of claim 1, wherein said at least one coating layer includes a patterned layer.

14. The bone implant of claim 13, wherein said patterned layer is a patterned layer including said apertures.

15. The bone implant of claim 14, wherein apertures of said aperture-patterned layer are arranged in an irregular pattern.

16. The bone implant of claim 1, further including a radio-opaque layer embedded within said body.

17. The bone implant of claim 16, wherein said radio-opaque layer is configured to at least one of:

minimize artifacts in magnetic resonance imaging (MRI) images; and reduce artifacts affecting tissue visualization in MRI images.

18. A method for manufacturing a bone implant comprising:

forming a body of fiber-reinforced polymer composite construction, wherein said forming a body includes embedding a radio-opaque layer within said fiber-reinforced polymer composite of said body, and wherein said embedding includes selecting at least one of an aperture size and a spacing of said radio-opaque layer to at least one of:

minimize artifacts in magnetic resonance imaging (MRI) images; and reduce artifacts affecting tissue visualization in MRI images;

preparing at least one coating layer for the bone implant; and attaching together the body and the prepared at least one coating layer; such that the at least one porous coating layer is restrained against the surface of said body.

19. The method of claim 18, wherein said at least one coating layer includes at least one of titanium (Ti), titanium nitride (TiN), titanium aluminum nitride Ti—Al—N), a titanium ceramic, a titanium alloy, and titanium oxide.

20. The method of claim 18, wherein said preparing includes 3-D printing said at least one coating layer on said body.

21. The method of claim 18, wherein said attaching includes compression molding.

22. The method of claim 21, wherein said compression molding is performed in a plurality of compression molding steps.

23. The method of claim 21, wherein said compression molding includes applying at least one of pressure and temperature to said at least one coating layer.

* * * * *